US007247456B2

(12) United States Patent
Sjoberg

(10) Patent No.: US 7,247,456 B2
(45) Date of Patent: Jul. 24, 2007

(54) PREPARATION OF FUCOSYLATED OLIGOSACCHARIDES

(75) Inventor: Eric R. Sjoberg, San Diego, CA (US)

(73) Assignee: Neose Technologies, Inc., Horsham, PA (US)

( * ) Notice: Subject to any disclaimer, the term of this patent is extended or adjusted under 35 U.S.C. 154(b) by 1003 days.

(21) Appl. No.: 10/206,425

(22) Filed: Jul. 25, 2002

(65) Prior Publication Data
US 2006/0234354 A1 Oct. 19, 2006

Related U.S. Application Data

(62) Division of application No. 09/231,905, filed on Jan. 14, 1999, now Pat. No. 6,500,661.

(60) Provisional application No. 60/071,076, filed on Jan. 15, 1998.

(51) Int. Cl.
C12P 19/04 (2006.01)
C12P 19/18 (2006.01)
C12N 9/02 (2006.01)
C12N 9/90 (2006.01)
C07H 21/04 (2006.01)

(52) U.S. Cl. .................. 435/72; 435/97; 435/101; 435/189; 435/233; 536/23.2

(58) Field of Classification Search .................. None
See application file for complete search history.

(56) References Cited

U.S. PATENT DOCUMENTS 5,352,670 A 10/1994 Venot et al.
5,374,541 A 12/1994 Wong et al.
5,374,655 A 12/1994 Kashem et al.
5,728,568 A 3/1998 Sullivan et al.

OTHER PUBLICATIONS

Tonetti et al (Jul. 1, 1998). Acta Cryst. D 54, pp. 684-686.*
Rizzi et al (Nov. 15, 1998).Structure, vol. 6, pp. 1453-1465.*
13 slides from presentation by Joachim Theim, May 1998, International GlycoBioTechnology Symposium 1998, Braunschweig, Germany.
Adrianopoulos, K. et al., "Identification of the fucose synthetase gene in the colonic acid gene cluster of Escherichia coli K-12," J. of Bacteriol., 1998, pp. 998-1001, vol. 180(4).
Berg, et al., "A carbohydrate domain common to both sialyl le$^a$ and sialyl le$^x$ is recognized by the endothelial cell leukocyte adhesion molecule ELAM-1," J. Biol. Chem., 1991, pp. 14869-14872, vol. 266.
Broschat, et al., "Purification and characterization of GDP-D-mannose 4,6-dehydratase from porcine thyroid," Eur. J. Biochem., 1985, pp. 397-401, vol. 153.
Cameron, et al., "Expression of human chromosome 19p α(1,3)-fucosyltransferase genes in normal tissues," J. of Biol. Chem., 1995, pp. 20112-20122, vol. 270.

Chang, S. et al., "An epimerase-reductase in L-fucose synthesis," J. Biol. Chem., 1988, pp. 1693-1697, vol. 263.
Dumas, et al., "Enzymatic synthesis of sialyl le$^x$ and derivatives based on a recombinant fucosyltransferase," Bioorg. Med. Letters, 1991, pp. 425-428, vol. 1.
Ge, et al., "Cloning and heterologous expression of an α1,3-fucosyltransferase gene from the gastric pathogen helicobacter pylori," J. Biol. Chem., 1997, pp. 21357-21363, vol. 272.
Ito, et al., "Synthesis of bioactive sialosides," Pure and Appl. Chem., 1993, pp. 753-760, vol. 65.
Kukowska-Latallo, et al., "A cloned human cDNA determines expression of a mouse stage-specific embryonic antigen and the Lewis blook group α(1,3/1,4)fucosyltransferase," Genes Dev., 1990, pp. 1288-1303, vol. 4.
Kumar, et al., "Cloning of a human α(1,3)-fucosyltransferase gene that encodes ELFT but does not confer fucosyltransferase cDNA that can form the H blook group antigen," J. Biol. Chem., 1991, pp. 21777-21783, vol. 266.
Larsen, et al., "Molecular cloning, sequence, and expression of a human GDP-L-fucose:β-D-galactoside 2- α-L-fucosyltransferase cDNA that can form the H blood group antigen," Proc. Nat'l. Acad. Sci. USA, 1990, pp. 6675-6678, vol. 87.
Mollicone, et al., "Acceptor specificity and tissue distribution of three human α-3-fucosyltransferases," Eur. J. Biochem., 1990, pp. 169-176, vol. 191.
Nunez, et al., "The synthesis and characterization of α- and β-L-fucopyranosyl phosphates and GDP fucose," Can. J. Chem., 1981, pp. 2086-2095, vol. 59.
Ohyama et al., "Molecular cloning and expression of GDP-D-mannose-4,6-dehydratase, a key enzyme for fucose metabolism defective in Lec13 cells," J. Biol. Chem., Jun. 1998, pp. 14582-14587, vol. 273(23).
Palcic, et al., "Enzymic synthesis of oligosaccharides terminating in the tumor-associated sialyl-lewis-a-deteminant," Carbohydrate Res., 1989, pp. 1-11, vol. 190.
Prieels, et al., "Co-purification of the lewis blood group N-acetylglucosaminide α1→4 fucosyltransferase and an N-acetylglucosaminide α 1→3 fucosyltransferase from human milk," J. Biol. Chem., 1981, pp. 10456-10463, vol. 256.
Reeves, P.R. et al., "Bacterial polysaccharide synthesis and gene nomenclature," Trends Microbiol., Dec. 1996, pp. 495-503, vol. 4(12).
Samesto, et al., "Purification of the β-N-acetylglucosaminide α1→3-fucosyltransferase from human serum," J. Biol. Chem., 1992, pp. 2745-2752, vol. 267.
Shinoda, et al., "Enzymatic characterization of human α1,3-fucosyltransferase fuc-TVII synthesized in a B cell lymphoma cell line," J. Biol. Chem., 1997, pp. 31992-31997, vol. 272, (Continued)

Primary Examiner—Elizabeth Slobodyansky
(74) Attorney, Agent, or Firm—Townsend and Townsend and Crew LLP

(57) ABSTRACT

This invention provides methods for practical enzymatic conversion of GDP-mannose to GDP-fucose. These methods are useful for efficient synthesis of reactants used in the synthesis of fucosylated oligosaccharides.

11 Claims, 12 Drawing Sheets

OTHER PUBLICATIONS

Staudacher, E., "α 1,3-fucosyltransferases," TIGG, 1996, pp. 391-408, vol. 8.

Stevenson, G. et al., "Organization of the *Escherichia coli* K-12 gene cluster responsible for production of the extracellular polysaccharide colani acid," J. of Bacteriol., 1996, pp. 4885-4893, vol. 178(16).

Sullivan, F.X. et al., "Molecular cloning of human GDP-mannose 4,6-dehydratase and rconstruction of GDP-lucose biosynthesis in vitro," J. of Biol. Chem., 1998, pp. 8193-8202, vol. 23(14).

Tonetti, M. et al., "Synthesis of GDP-L-fucose by the human FX protein," J. of Biochem. Chem., 1996, pp. 27274-27279, vol. 271(44).

Weston, et al., "Isolation of a novel human α(1,3) fucosyltransferase gene and molecular comparison to the human Lewis blood group α(1,3/1,4) fucosyltransferase gene," J. Biol. Chem., 1992, pp. 4152-4160, vol. 267.

Weston, et al., "Molecular cloning of a fourth member of a human α(1,3)fucosyltransferase gene family," J. Biol. Chem., 1992, pp. 24575-24584, vol. 267.

Wong et. al., J. Am. Chem. Soc., 1985, pp. 4028-4031, vol. 107.

Frick, David N.; "A Novel GDP-Mannose Mannosyl Hydrolase Shares Homology with the MutT Family of Enzymes"; The Journal of Biological Chemistry; 1995; pp. 24086-24091; vol. 270, No. 41.

* cited by examiner

Conversion of GDP-mannose to GDP-fucose

GDP-Mannose Half Fucosyltransferase Cycle

Mannose Full Fucosyltransferase Cycle

PREPARATION OF FUCOSYLATED OLIGOSACCHARIDES

This is a divisional application of and claims the benefit of U.S. patent application Ser. No. 09/231,905, filed Jan. 14, 1999, now U.S. Pat. No. 6,500,661 which claims the benefit of U.S. Provisional Application No. 60/071,076, filed Jan. 15, 1998, which application is incorporated herein by reference for all purposes.

BACKGROUND OF THE INVENTION

1. Field of the Invention

The present invention relates to the synthesis of oligosaccharides. In particular, it relates to improved enzymatic synthesis of GDP-fucose, which can be used in fucosylation reactions. The methods make possible the synthesis of complex fucosylated oligosaccharides in a single vessel using readily available starting materials.

2. Background

Increased understanding of the role of carbohydrates as recognition elements on the surface of cells has led to increased interest in the production of carbohydrate molecules of defined structure. For instance, compounds comprising the sialyl Lewis ligands, sialyl Lewis$^x$ and sialyl Lewis$^a$ are present in leukocyte and non-leukocyte cell lines that bind to receptors such as the ELAM-1 and GMP 140 receptors. Polley et al., *Proc. Natl. Acad. Sci., USA,* 88: 6224 (1991) and Phillips et al., *Science,* 250: 1130 (1990), see, also, U.S. Ser. No. 08/063,181.

Because of interest in making desired carbohydrate structures, glycosyltransferases and their role in enzyme-catalyzed synthesis of carbohydrates are presently being extensively studied. These enzymes exhibit high specificity and are useful in forming carbohydrate structures of defined sequence. Consequently, glycosyltransferases are increasingly used as enzymatic catalysts in synthesis of a number of carbohydrates used for therapeutic and other purposes.

In the application of enzymes to the field of synthetic carbohydrate chemistry, the use of glycosyltransferases for enzymatic synthesis of carbohydrate offers advantages over chemical methods due to the virtually complete stereoselectivity and linkage specificity offered by the enzymes (Ito et al., *Pure Appl. Chem.,* 65:753 (1993); and U.S. Pat. Nos. 5,352,670, and 5,374,541). However, the commercial-scale production of carbohydrate compounds is often complicated by the cost and difficulty in obtaining reactants that are used in the enzymatic and chemical synthesis of the carbohydrates.

Improved methods for enzymatic synthesis of carbohydrate compounds, and precursors used in these syntheses, would advance the production of a number of beneficial compounds. The present invention fulfills these and other needs.

SUMMARY OF THE INVENTION

The present invention provides methods, expression vectors, and reaction mixtures that are useful for the efficient production of fucosylated oligosaccharides. The invention provides ways by which nucleotide sugars such as GDP-fucose can be formed relatively inexpensively.

In a first embodiment, the invention provides expression vectors that include a promoter operably linked to a nucleic acid that encodes a prokaryotic enzyme that has both an epimerase and a reductase activity. These two activities catalyze the conversion of GDP-4-keto-6-deoxymannose to GDP-fucose.

In another embodiment, the invention provides a reaction mixture for synthesizing GDP-fucose. The reaction mixture includes GDP-4-keto-6-deoxymannose, NADPH, and a prokaryotic enzyme that has both an epimerase and a reductase activity. The prokaryotic enzyme can catalyze the conversion of GDP-4-keto-6-deoxymannose to GDP-fucose. In a presently preferred embodiment, the GDP-4-keto-6-deoxymannose is formed by: a) providing a reaction mixture that comprises GDP-mannose, GDP-mannose-4,6-dehydratase, and NADP$^+$; and b) incubating the reaction mixture for a sufficient time to convert at least about 90% of the GDP-mannose to GDP-4-keto-6-deoxymannose.

Another embodiment of the invention provides methods for the enzymatic conversion of GDP-mannose to GDP-fucose. These methods involve:

a) providing a reaction mixture that comprises GDP-mannose, GDP-mannose 4,6-dehydratase, and NADP$^+$;

b) incubating the reaction mixture for a sufficient time to convert at least about 90% of the GDP-mannose to GDP-4-keto-6-deoxymannose;

c) adding to the reaction mixture one or more polypeptides having GDP-4-keto-6-deoxymannose 3,5-epimerase and GDP-4-keto-6-galactose reductase activities; and d) incubating the reaction mixture for a sufficient time to convert the GDP-4-keto-6-deoxymannose to GDP-fucose.

Also provided are methods for enzymatic synthesis of a fucosylated oligosaccharide. These methods involve transferring a fucose from the GDP-fucose produced by the methods of the invention to an acceptor saccharide. This can be accomplished by the following additional steps: e) adding a fucosyltransferase and the acceptor saccharide to the GDP-4-keto-6-deoxymannose produced in step b) or to the GDP-fucose produced in step d); and f) incubating a reaction mixture for a sufficient time to transfer the fucose from the GDP-fucose to the acceptor saccharide.

Additional embodiments provide methods by which one can generate GDP-fucose starting from mannose. These methods involve the use of an enzymatic system for converting mannose into GDP-mannose, which is then converted to GDP-fucose using the above methods. The conversion of mannose to GDP-mannose involves the following enzymes: hexokinase, which converts mannose to mannose-6-phosphate; phosphomannomutase, which converts the mannose-6-phosphate to mannose-1-phosphate; and GDP-mannose pyrophosphorylase, which converts the mannose-1-phosphate to GDP-mannose.

Also provided by the invention are methods for the synthesis of a fucosylated oligosaccharide in which efficiency-enhancing steps are used. The methods involve contacting an acceptor saccharide with a fucosylation reaction mixture that comprises GDP-fucose and a fucosyltransferase which transfers fucose from the GDP-fucose to provide said fucosylated oligosaccharide, wherein the efficiency of said fucosylation is enhanced by one or more efficiency-enhancing steps selected from the group consisting of:

1) forming said GDP-fucose by enzymatic conversion of GDP-mannose to GDP-fucose by:

a) providing a reaction mixture that comprises GDP-mannose, GDP-mannose 4,6-dehydratase, and NADP$^+$;

b) incubating the reaction mixture for a sufficient time to convert at least about 90% of the GDP-mannose to GDP-4-keto-6-deoxymannose;

c) adding to the product of step b) one or more polypeptides having GDP-4-keto-6-deoxymannose 3,5-epimerase and GDP-4-keto-6-galactose reductase activities; and d) incubating the reaction mixture for a sufficient time to convert the GDP-4-keto-6-deoxymannose to GDP-fucose;

2) adding pyruvate kinase and a substrate for the pyruvate kinase to the fucosylation reaction mixture, wherein GDP produced as a result of the transfer of fucose from the GDP-fucose is converted to GTP; and 3) conducting the fucosylation in a reaction medium that comprises a soluble divalent metal cation, wherein said medium is supplemented with said soluble divalent metal cation to maintain the concentration of said divalent metal cation between about 2 mM and about 75 mM.

DETAILED DESCRIPTION

Definitions

Figure 1:
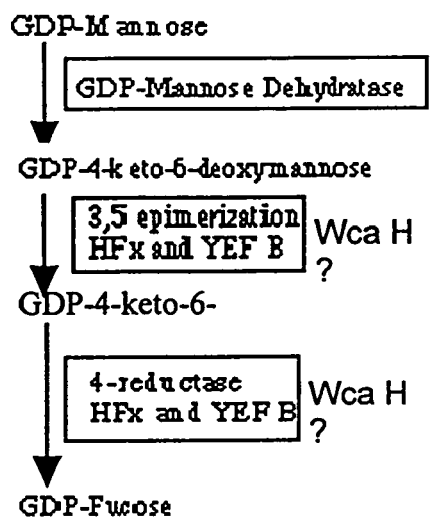
FIG. 1 shows a schematic diagram of the enzymatic conversion of GDP-mannose to GDP-fucose.

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

The following abbreviations for carbohydrate compounds are used herein:

| | |
|---|---|
| Ara = | arabinosyl; |
| Fru = | fructosyl; |
| Fuc = | fucosyl; |
| Gal = | galactosyl; |
| GalNAc = | N-acetylgalactosaminyl; |
| Glc = | glucosyl; |
| GlcNAc = | N-acetylglucosaminyl; |
| Man = | mannosyl; and |
| Sia (NeuAc) = | sialyl (typically N-acetylneuraminyl). |

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al. (1990) *J. Biol. Chem.* 265: 21811-21819. Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 25-40; *Sialic Acids: Chemistry, Metabolism and Function*, R. Schauer, Ed.

(Springer-Verlag, New York (1992)). The synthesis and use of sialic acid compounds in a sialylation procedure is disclosed in international application WO 92/16640, published Oct. 1, 1992.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contains nucleic acid endogenous to the cell that has been modified without removing the nucleic acid from the cell; such modifications include those obtained by gene replacement, site-specific mutation, and related techniques. A "recombinant polypeptide" is one which has been produced by a recombinant cell.

A "recombinant expression cassette" or simply an "expression cassette" is a nucleic acid construct, generated recombinantly or synthetically, with nucleic acid elements that are capable of effecting expression of a structural gene in hosts compatible with such control elements. Expression cassettes include at least promoters and optionally, transcription termination signals. Typically, the recombinant expression cassette includes a nucleic acid to be transcribed (e.g., a nucleic acid encoding a desired polypeptide), and a promoter (e.g., a dual promoter that contains a tac promoter component and a gal promoter component as described in PCT/US97/20528; Int'l. Publ. No. WO 9820111) that is operably linked to the nucleic acid. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "heterologous sequence" or a "heterologous nucleic acid", as used herein, is one that originates from a source foreign to the particular host cell (e.g., from a different species), or, if from the same source, is modified from its original form. Thus, a heterologous nucleic acid operably linked to a promoter is from a source different from that from which the promoter was derived, or, if from the same source, is modified from its original form. For example, a UDPglucose 4-epimerase gene promoter can be linked to a structural gene encoding a polypeptide other than native UDPglucose 4-epimerase. A heterologous gene that encodes an enzyme involved in conversion of GDP-mannose to GDP-fucose, for example, in a prokaryotic host cell includes a gene that is endogenous to the particular host cell that has been modified. Modification of the heterologous nucleic acid can occur, e.g., by treating the DNA with a restriction enzyme to generate a DNA fragment that is capable of being operably linked to the promoter. Techniques such as site-directed mutagenesis are also useful for modifying a heterologous nucleic acid.

A "subsequence" refers to a sequence of nucleic acids or amino acids that comprise a part of a longer sequence of nucleic acids or amino acids (e.g., polypeptide) respectively.

The term "isolated" is meant to refer to material which is substantially or essentially free from components which normally accompany the nucleic acid, polypeptide, or other molecule as found in its native state. Typically, isolated molecules are at least about 80% pure, usually at least about 90%, and preferably at least about 95% pure as measured by, e.g., band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1997) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of the GDP-fucose-synthesizing enzymes and nucleic acid that encode the enzymes yield essentially identical products. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. As described herein, sequences are preferably optimized for expression in a particular host cell used to produce the enzyme (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

DESCRIPTION OF THE PREFERRED EMBODIMENTS

The present invention provides methods for efficient production of substrates such as nucleotide sugars (e.g., GDP-fucose) that are useful in synthesis of fucosylated carbohydrate compounds. Expression vectors for producing enzymes that are used in these methods are also provided. Methods for using these enzymes and methods for producing nucleotide sugars to produce fucosylated oligosaccharides are also provided by the invention.

The methods of the invention provide significant advantages over previously available methods for fucosylation. For example, the methods provide a relatively inexpensive way to make GDP-fucose, an expensive compound, starting from the lower-cost GDP-mannose, or even from mannose. The invention provides methods by which the efficiency of the GDP-fucose synthesis, and also the efficiency of subsequent fucosyltransferase reactions, can be improved. The methods of the invention provide a high yield of the desired fucosylated compound. Accordingly, the methods of the invention are well suited for commercial-scale production of fucosylated compounds, including those that are useful for diagnostic and therapeutic uses, foodstuffs, and the like.

A. Cloning and Expression of Nucleic Acids Encoding Enzymes Useful for Conversion of GDP-Mannose to GDP-Fucose The invention provides, in a first embodiment, methods of producing enzymes that are useful for converting GDP-mannose to GDP-fucose. This biosynthetic pathway, which is diagrammed in FIG. 1, involves three enzymatic activities. The first enzyme, GDP-mannose dehydratase catalyzes the conversion of GDP-mannose to GDP-4-keto-6-D-deoxymannose. This product is then epimerized to GDP-4-keto-6-L-deoxygalactose, which is in turn reduced to GDP-L-fucose by a 4' reductase. The latter two enzymatic activities (epimerase and reductase) are both found in the human Fx protein (Tonetti et al. (1996) *J. Biol. Chem.* 271: 27274-27279; GenBank Accession No. U58766).

For use in commercial-scale enzymatic synthetic reactions, however, it is preferred to use enzymes that are readily produced in prokaryotes, which are much easier and more efficient to grow at large scale than mammalian cells. Mammalian enzymes are often not expressed in the proper form at high yields when genes for the mammalian enzymes are inserted into prokaryotic host cells. Thus, it was of great interest to obtain a prokaryotic enzyme or enzymes to catalyze the epimerization and reduction. However, prior to the instant invention, it was not known whether bacterial systems for GDP-fucose synthesis required one or two separate polypeptides to catalyze the epimerization and reduction of GDP-4-keto-6-D-deoxymannose to GDP-fucose. The present invention provides this missing information, demonstrating that one enzyme catalyzes both of these activities. In *E. coli*, this enzyme is designated YEF B. The need to produce only one enzyme to catalyze two activities simplifies the development and scale-up of GDP-fucose production.

Accordingly, the present invention provides methods and vectors for recombinant production of enzymes that are useful for producing GDP-fucose. Recombinant production of a polypeptide generally involves obtaining a DNA sequence that encodes the particular enzyme, modified as desired, placing the DNA in an expression cassette under the control of a particular promoter, expressing the protein in a host, isolating the expressed protein and, if required, renaturing the protein. More than one of the enzymes can be expressed in the same host cells, either on the same expression vector or on more than one expression vector that is present in the cells.

In one embodiment, the invention provides expression vectors that are useful in methods for producing enzymes involved in GDP-fucose synthesis in a host cell. For example, expression vectors are provided that are useful for expressing YEF B of *E. coli*, which catalyzes the both the epimerization and reduction of GDP-4-keto-6-deoxymannose to obtain GDP-fucose. The expression vectors can also express related enzymes, in particular those from other prokaryotes, that also have the dual epimerase/reductase activity.

1. Epimerase/Reductase-Encoding Nucleic Acids

The expression vectors of the invention include a nucleic acid that encodes an enzyme that has both GDP-4-keto-6-D-deoxymannose epimerase activity and GDP-4-keto-6-L-deoxygalactose reductase activity. A prokaryotic enzyme is encoded by the nucleic acid in presently preferred embodiments. For example, one can use a nucleic acid that encodes a prokaryotic epimerase/reductase from any prokaryotic species, including *E. coli*. The enzyme can be, for example, substantially identical to an *E. coli* YEF B polypeptide. In some embodiments, the expression vectors include a nucleic acid that encodes an epimerase/reductase enzyme that has an amino acid sequence as shown in SEQ ID NO: 1. The nucleic acids can also encode polypeptides that have conservative amino acid substitutions compared to the amino acid sequence of a native epimerase/reductase enzyme, such as the *E. coli* YEF B enzyme. Typically, the nucleic acids used in the expression vectors of the invention are at least about 75% identical to the nucleic acid sequence of the *E. coli* YEF B coding region as shown in GenBank Accession No. U38473 (nucleotides 10748 to 11230). More preferably, the nucleic acids used in the expression vectors are at least about 85% identical to the *E. coli* YEF B coding region, and still more preferably are at least about 95% identical. Typically, a computerized algorithm such as BLAST is used for the comparison, preferably using default parameters. These percentage identities can be an overall value for the entire coding regions, or can refer to the percentage identity over a particular region of the coding regions. For example, in a presently preferred embodiment, the nucleic acids used in the expression vectors of the invention are at least about 85% identical over a region of at least 40 nucleotides in length, using a pairwise BLAST algorithm (BLASTN 2.0.6 as implemented by the National Center for Biotechnology Information) with the following parameters: Match: 1; Mismatch: −2, Gap open: 5; Gap extension: 2, x-dropoff: 50; expect: 10.00; wordsize: 11; with no filtering.

The nucleic acids that encode the epimerase/reductase enzyme can be obtained using methods that are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017, 478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426, 039.

Nucleic acids that encode enzymes having both epimerase and reductase activities, or subsequences of these nucleic acids, can be prepared by any suitable method as described above, including, for example, cloning and restriction of appropriate sequences. As an example, one can obtain a nucleic acid that encodes a polypeptide that has both epimerase and reductase activities by routine cloning methods. A nucleotide sequence of a gene that encodes an enzyme known to have both activities, such as a YEF B enzyme, can be used to provide probes that specifically hybridize to a gene that encodes a suitable enzyme in a genomic DNA sample, or to a mRNA in a total RNA sample (e.g., in a Southern or Northern blot). Suitable sequences are provided in, for example, GenBank or other sequence database.

One suitable nucleotide sequence for use as a probe or in an expression vector of the invention is found in an *E. coli* gene cluster that encodes GDP-fucose-synthesizing enzymes as described by Stevenson et al. (1996) *J. Bacteriol.* 178: 4885-4893 (GenBank Accession No. U38473). This gene cluster had been reported to include an open reading frame for GDP-mannose dehydratase (nucleotides 8659-9780 in GenBank Accession No. U38473). Applicants discovered that this gene cluster also contains an open reading frame that encodes an enzyme that has both 3,5 epimerization and 4-reductase activities (FIG. 1), and thus is capable of converting the product of the GDP-mannose dehydratase reaction (GDP-4-keto-6-deoxymannose) to GDP-fucose. This ORF, which is designated YEF B, wcaG, and fcl, is found at nucleotides 9783-10748 of GenBank Accession No. U38473. Prior to Applicants' discovery that YEF B encodes an enzyme having two activities, it was not known whether one or two enzymes were required for conversion of GDP-4-keto-6-deoxymannose to GDP-fucose by prokaryotes.

The gene cluster from *E. coli* includes an additional ORF, which is designated wcaH (nucleotides 10748-11230 of GenBank Accession No. U38473). This small open reading frame, which encodes a GDP-mannose mannosyl hydrolase of 15 kd, is located just downstream of the YEF B coding region (designated wcaG). Each of these enzymes was expressed in bacteria as assessed by SDS-PAGE and ability to form GDP-fucose from GDP-mannose.

Once the target epimerase/reductase nucleic acid is identified, it can be isolated according to standard methods known to those of skill in the art (see, e.g., Sambrook et al. (1989) *Molecular Cloning: A Laboratory Manual, 2nd Ed., Vols.* 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York).

A nucleic acid that encodes a prokaryotic epimerase/reductase can also be cloned by detecting its expressed product by means of assays based on the physical, chemical, or immunological properties. For example, one can identify a cloned epimerase/reductase-encoding nucleic acid by the ability of a polypeptide encoded by the nucleic acid to catalyze the conversion of GDP-4-keto-4-deoxymannose to GDP-fucose. In a preferred method, reverse phase HPLC is used to determine the amounts of GDP-mannose, GDP-fucose, and optionally one or more intermediates (e.g., GDP-4-keto-6-deoxymannose and GDP-4-keto-6-deoxygalactose) at various times of reaction. Suitable assay conditions are described in the Examples.

In one embodiment, epimerase/reductase-encoding nucleic acids can be cloned using DNA amplification methods such as polymerase chain reaction (PCR). Thus, for example, the nucleic acid sequence or subsequence is PCR amplified, using a sense primer containing one restriction site (e.g., XbaI) and an antisense primer containing another restriction site (e.g., HindIII). This will produce a nucleic acid encoding the desired epimerase/reductase amino acid sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided in GenBank or other sources. Appropriate restriction sites can also be added to the nucleic acid encoding the epimerase/ reductase or amino acid subsequence by site-directed mutagenesis. The plasmid containing the epimerase/reductase-encoding nucleotide sequence or subsequence is cleaved with the appropriate restriction endonuclease and then ligated into an appropriate vector for amplification and/or expression according to standard methods.

Examples of suitable primers suitable for amplification of GDP-fucose-synthesizing enzymes are shown in Table 1; each primer pair is designed to provide a 5' XbaI restriction site and a 3' HindIII site on the amplified fragment. The plasmid containing the enzyme-encoding sequence or subsequence is cleaved with the appropriate restriction endonuclease and then ligated into an appropriate vector for amplification and/or expression according to standard methods.

TABLE 1

| Enzyme | 5' Primer | 3' Primer |
|---|---|---|
| GDP-mannose dehydratase (E. coli) | 5'-CGCTCTAGATACATGT CAAAAGTCGCT-3' (SEQ ID NO:2) | 5'-GCGAAGCTTTTATGA CTCCAGCGCGAT-3' (SEQ ID NO:3) |
| YEF B (E. coli) | 5'-CGTCCTAGAGCGAT GAGTAAACAACGAGTT-3' (SEQ ID NO:4) | 5'-GCGAAGCTTTTACCCCC GAAAGCGGTC-3' (SEQ ID NO:5) |
| Wca H (E. coli) | 5'-GCTCTAGAGTAATGA TGTTTTTACGTCAGG-3' (SEQ ID NO:6) | 5'-CCCAAGCTTTCATAAT CCGGGTACTCCGGT-3' (SEQ ID NO:7) |
| Fx (human) | 5'-GCTCTAGAGACATG GGTGAACCCCAGGGAT-3' (SEQ ID NO:8) | 5'-ACGAAGCTTCACTTCC GGGCCTGCTCGTAGTTG-3' (SEQ ID NO:9) |

As an alternative to cloning an epimerase/reductase-encoding nucleic acid, a suitable nucleic acid can be chemically synthesized from a known sequence that encodes a YEF B polypeptide or a related enzyme that has both epimerase and reductase activities. Direct chemical synthesis methods include, for example, the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences. Alternatively, subsequences may be cloned and the appropriate subsequences cleaved using appropriate restriction enzymes. The fragments may then be ligated to produce the desired DNA sequence.

A nucleic acid encoding a GDP-fucose-synthesizing enzyme can be identified by detecting its expressed product by means of assays based on the physical, chemical, or immunological properties. For example, one can identify a cloned GDP-fucose-synthesizing nucleic acid by the ability of a polypeptide encoded by the nucleic acid to catalyze the conversion of GDP-mannose to GDP-fucose. Other physical properties of a polypeptide expressed from a particular nucleic acid can be compared to properties of known YEF B-like polypeptides to provide another method of identifying epimerase/reductase-encoding nucleic acids. Alternatively, a putative epimerase/reductase gene can be mutated, and its role as an epimerase/reductase established by detecting a variation in the ability to produce GDP-fucose.

In some embodiments, it may be desirable to modify the epimerase/reductase-encoding nucleic acids. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

In a preferred embodiment, the recombinant nucleic acids present in the cells of the invention are modified to provide preferred codons which enhance translation of the nucleic acid in a selected organism (e.g., yeast preferred codons are substituted into a coding nucleic acid for expression in yeast).

2. Expression Vectors and Methods for Expressing Enzymes Involved in GDP-Fucose Synthesis The invention provides expression cassettes, and expression vectors containing the cassettes, that are useful for expressing the GDP-fucose synthesizing enzymes, in particular polypeptides that have both epimerase and reductase activities. These expression cassettes include the nucleic acids encoding GDP-fucose-synthesizing enzymes, which are operably linked to a promoter that is functional in a desired host cell. The expression cassettes can also include other sequences involved in transcription, translation, and post-translational modification of the enzyme. Such sequences are described in more detail below. The invention also provides expression vectors, and host cells that comprise the recombinant nucleic acids described herein.

Typically, the polynucleotide that encodes the enzyme involved in nucleotide sugar synthesis is placed under the control of a promoter that is functional in the desired host cell. An extremely wide variety of promoters are well known, and can be used in the vectors of the invention, depending on the particular application. Ordinarily, the promoter selected depends upon the cell in which the promoter is to be active. Other expression control sequences such as ribosome binding sites, transcription termination sites and the like are also optionally included. Expression control sequences that are suitable for use in a particular host cell are often obtained by cloning a gene that is expressed in that cell.

In another embodiment, the invention provides recombinant cells that are useful for producing enzymes that catalyze one or more steps in the conversion of GDP-mannose to GDP-fucose. The recombinant cells contain an expression cassette, preferably included on an expression vector (unless the expression cassette is integrated into the genome of the host cell). Host cells of the invention can be plant cells or microorganisms, such as, for example, yeast cells, bacterial cells, or fungal cells. Examples of suitable cells include, for example, *Azotobacter* sp. (e.g., *A. vinelandii*), *Pseudomonas* sp., *Rhizobium* sp., *Erwinia* sp., *Escherichia* sp. (e.g., *E. coli*), and *Klebsiella* sp., among many others. The cells can be of any of several genera, including *Saccharomyces* (e.g., *S. cerevisiae*), *Candida* (e.g. *C. utilis*, *C. parapsilosis*, *C. krusei*, *C. versatilis*, *C. lipolytica*, *C. zeylanoides*, *C. guilliermondii*, *C. albicans*, and *C. humicola*), *Pichia* (e.g., *P. farinosa* and *P. ohmeri*), *Torulopsis* (e.g., *T. candida*, *T.*

*sphaerica, T. xylinus, T. famata*, and *T. versatilis*), *Debaryomyces* (e.g., *D. subglobosus, D. cantarelii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*).

A promoter and other control signals can be derived from a gene that is under investigation, or can be a heterologous promoter or other signal that is obtained from a different gene, or from a different species. Where continuous expression of a gene is desired, one can use a "constitutive" promoter, which is generally active under most environmental conditions and states of development or cell differentiation. Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, *Arabidopsis* (Sun and Callis, *Plant J.*, 11(5):1017-1027 (1997)), the mas, Mac or DoubleMac promoters (described in U.S. Pat. No. 5,106,739 and by Comai et al., *Plant Mol. Biol.* 15:373-381 (1990)) and other transcription initiation regions from various plant genes known to those of skill in the art. Such genes include for example, ACT11 from *Arabidopsis* (Huang et al., *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al., *Plant Physiol.* 104:1167-1176 (1994)), GPc1 from maize (GenBank No. X15596, Martinez et al., *J. Mol. Biol.* 208: 551-565 (1989)), and Gpc2 from maize (GenBank No. U45855, Manjunath et al., *Plant Mol. Biol.* 33:97-112 (1997)). Useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the (α-conglycinin promoter, the phaseolin promoter, the ADH promoter, and heat-shock promoters.

Promoters for use in *E. coli* include the T7, trp, or lambda promoters. A ribosome binding site and preferably a transcription termination signal are also provided. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences.

In yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

In some embodiments, the polynucleotides are placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT/US97/20528 (Int'l. Publ. No. WO 9820111), provides a level of expression that is greater than that provided by either promoter alone.

Inducible promoters for use in plants are known to those of skill in the art (see, e.g., references cited in Kuhlemeier et al (1987) *Ann. Rev. Plant Physiol.* 38:221), and include those of the 1,5-ribulose bisphosphate carboxylase small subunit genes of *Arabidopsis thaliana* (the "ssu" promoter), which are light-inducible and active only in photosynthetic tissue, anther-specific promoters (EP 344029), and seed-specific promoters of, for example, *Arabidopsis thaliana* (Krebbers et al. (1988) *Plant Physiol.* 87:859).

Inducible promoters for other organisms are also well known to those of skill in the art. These include, for example, the arabinose promoter, the lacZ promoter, the metallothionein promoter, and the heat shock promoter, as well as many others.

A construct that includes a polynucleotide of interest operably linked to gene expression control signals that, when placed in an appropriate host cell, drive expression of the polynucleotide is termed an "expression cassette." Expression cassettes that encode the YEF B and/or other enzyme involved in nucleotide sugar synthesis are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT/US97/20528 (Int'l. Publ. No. WO 9820111).

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to construct the cells of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for *Bacilli*. Often, the vector will have one selectable marker that is functional in, e.g., *E. coli*, or other cells in which the vector is replicated prior to being introduced into the target cell. A number of selectable markers are known to those of skill in the art and are described for instance in Sambrook et al., supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) *Proc. Nat'l Acad. Sci. USA* 78: 2072; Southern & Berg (1982) *J. Mol. Appl. Genet.* 1: 327).

Selection markers for plant and/or other eukaryotic cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use in constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Suitable methods for introducing the expression vectors into a chosen host cell are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Once expressed, the recombinant GDP-fucose-synthesizing enzymes can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

In some embodiments, however, the enzymes are used in an unpurified state, e.g., as a cell lysate. The recombinant cells of the invention are grown in culture to obtain a sufficient number of cells for use in a reaction of a desired scale. Methods and culture media for growth of the respective host cells are well known to those of skill in the art. Culture can be conducted in, for example, aerated spinner or shaking culture, or, more preferably, in a fermentor. Upon growth of the recombinant cells to a desired cell density, the cells are typically processed for use in the reaction mixtures and methods of the invention. For example, the cells are generally permeabilized or otherwise disrupted to allow entry of the soluble saccharide acceptors into the cells. The YEF B or other enzyme produced by the cells can, in some situations, diffuse from the cells into the extracellular fluid. Methods of permeabilizing cells so as to not significantly degrade enzymatic activity are known to those of skill in the art. Cells can be subjected to concentration, drying, lyophilization, treatment with surfactants, ultrasonic treatment, mechanical disruption, enzymatic treatment, and the like.

The treated cells are then used in a reaction mixture that contains additional reactants, known to those of skill in the art, that are necessary or desirable for the enzymatic activity of the GDP-fucose-synthesizing enzyme. The concentration of treated cells used in the reaction mixture is typically between about 0.1% (wet wt/vol) and 40% (wet wt/vol), more preferably between about 1% (wet wt/vol) and about 20% (wet wt/vol), and most preferably between about 2% (wet wt/vol) and about 10% (wet wt/vol), or a corresponding amount of dry cells.

One of skill in the art would recognize that after chemical synthesis, biological expression, or purification, the GDP-fucose-synthesizing enzyme(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065-14070; Kreitman and Pastan (1993) *Bioconjug Chem.*, 4: 581-585; and Buchner, et al., (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine. One significant advantage of using a prokaryotic enzyme such as YEF B in a prokaryotic expression system, such as is used in a preferred embodiment of the instant invention, is that denaturation and refolding are not usually required. Active prokaryotic epimerase/reductase is obtained in large quantities without these additional steps.

One of skill would recognize that modifications can be made to the GDP-fucose-synthesizing enzymes without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

B. Enzymatic Conversion of GDP-Mannose to GDP-Fucose

The invention also provides methods enzymatically converting GDP-mannose to GDP-fucose. The methods often involve using one or more of GDP-mannose dehydratase (GMD) and epimerase/reductase enzymes. In presently preferred embodiments, the methods use a prokaryotic GMD enzyme, as well as a prokaryotic enzyme that has both epimerase and reductase activities. An example of a preferred enzyme that has both activities is the YEF B polypeptide of *E. coli*. In other embodiments, a eukaryotic enzyme such a human Fx protein can be used. The methods of the invention provide a means by which GDP-fucose can be produced efficiently and in high purity using relatively low-cost starting materials.

Several embodiments of the invention provide methods by which the efficiency of the GDP-mannose to GDP-fucose reaction can be increased substantially. In previously known methods, the enzymes in the enzymatic pathway are used in a coupled reaction, in which GDP-4-keto-6-deoxymannose is produced and simultaneously epimerized/reduced to obtain GDP-fucose. However, the GMD enzyme that catalyzes the initial step of the synthetic pathway, the conversion of GDP-mannose to GDP-4-keto-6-deoxymannose, was found to be strongly inhibited by GDP-fucose. At 50 µM GDP-fucose, GDP-mannose dehydratase possesses only 10% of its catalytic activity (Broschat et al (1985) *Eur. J. Biochem.* 153: 397-401). To avoid the reduction in yield caused by this product inhibition, the methods of the invention involve, in some embodiments, allowing the first step of the pathway to proceed nearly or completely to completion before adding the second enzyme of the pathway (e.g., the epimerase/reductase). In presently preferred embodiments, the conversion of GDP-mannose to GDP-4-keto-6-deoxymannose is at least about 80% complete, more preferably at least about 90% complete, and still more preferably at least about 95% complete, at the time the subsequent enzyme or enzymes is added to the reaction mixture. The reaction mixtures for the GMD-catalyzed reaction require the presence of $NADP^+$. In another embodiment, a fucosyltransferase and acceptor saccharide are added to the product of the GMD reaction, GDP-4-keto-6-deoxymannose along with the epimerase/reductase. The GDP-fucose formed by the epimerase/reductase is consumed by the fucosyltransferase, thus preventing the feedback inhibition of GMD.

The invention also provides reaction mixtures for enzymatic synthesis of GDP-fucose. In some embodiments, the reaction mixtures include GDP-4-keto-6-deoxymannose, NADPH or NADH, and one or more polypeptides that have epimerase activity and reductase activity (e.g., YEF B or a suitable analog), preferably from a prokaryote. The epimerase/reductase polypeptide catalyzes the epimerization and reduction of GDP 4-keto-6-deoxymannose to form GDP-fucose. The GDP-4-keto-deoxymannose is preferably obtained by GMD-catalyzed conversion from GDP-mannose as described above.

The epimerase/reduction to obtain GDP-fucose requires either NADPH or NADH. In some embodiments, one can employ a regenerating system by which the oxidized electron donor is regenerated to NADPH or NADH. For example, one can include in the reaction mixture an enzyme that utilizes $NADP^+$ or $NAD^+$ to oxidize a substrate for the enzyme, which substrate is also included in the reaction mixture. Examples of suitable recycling enzymes include, for example, alcohol dehydrogenase, glucose dehydrogenase, formate dehydrogenase, hydrogenase, and glucose-6-phosphate dehydrogenase (see, e.g., Wong et al. (1985) *J. Am. Chem. Soc.* 107: 4028-4031). In a presently preferred embodiment, glucose dehydrogenase and its substrate glucose are used to regenerate NADPH or NADH.

The invention also provides methods and reaction mixtures in which the GDP-fucose-synthesizing reactions are coupled to fucosyltransferase reactions in which the fucose residue is transferred from GDP-fucose to a suitable saccharide acceptor. A number of suitable fucosyltransferases are known to those of skill in the art. Briefly, fucosyltransferases include any of those enzymes which transfer L-fucose from GDP-fucose to a hydroxy position of an acceptor sugar. An example of an acceptable acceptor sugar is a GlcNAc in a βGal(1→4)βGlcNAc group in an oligosaccharide glycoside. Suitable fucosyltransferases then include the known βGal(1→3,4)βGlcNAc α(1→3,4)fucosyltransferase (FTIII E.C. No. 2.4.1.65) which can be obtained from human milk (see, Palcic, et al., *Carbohydrate Res.* 190:1-11 (1989); Prieels, et al., *J. Biol. Chem.* 256:10456-10463 (1981); and Nunez, et al., *Can. J. Chem.* 59:2086-2095 (1981)) and the βGal(1→4)βGlcNAc α(1→3)fucosyltransferases (FTIV, FTV, FTVI, and FTVII, E.C. No. 2.4.1.65)

which are found in human serum. A recombinant form of βGal(1→3,4)βGlcNAc α(1→3,4)fucosyltransferase is also available (see, Dumas, et al., *Bioorg. Med. Letters* 1:425-428 (1991) and Kukowska-Latallo, et al., *Genes and Development* 4:1288-1303 (1990)). Other exemplary fucosyltransferases include α1,2 fucosyltransferase (E.C. No. 2.4.1.69); additional fucosyltransferases are listed in Table 2. Enzymatic fucosylation may be carried out by the methods described in Mollicone, et al., *Eur. J. Biochem.* 191:169-176 (1990) or U.S. Pat. No. 5,374,655.

The invention also provides methods for improving the efficiency of fucosyltransferase-mediated transfer of fucose from GDP-fucose to an acceptor saccharide. One problem with coupled reactions in which GDP-mannose is converted to GDP-fucose, which is then nearly simultaneously transferred to an acceptor saccharide is that GDP inhibits both GMD and fucosyltransferase. Thus, in one embodiment, the methods of the invention involve improving the efficiency of fucosylated saccharide production by conducting the enzymatic synthesis of GDP-fucose separately from the fucosyltransferase reaction. Free GDP is not released, so the GMD is not inhibited.

Figure 9:
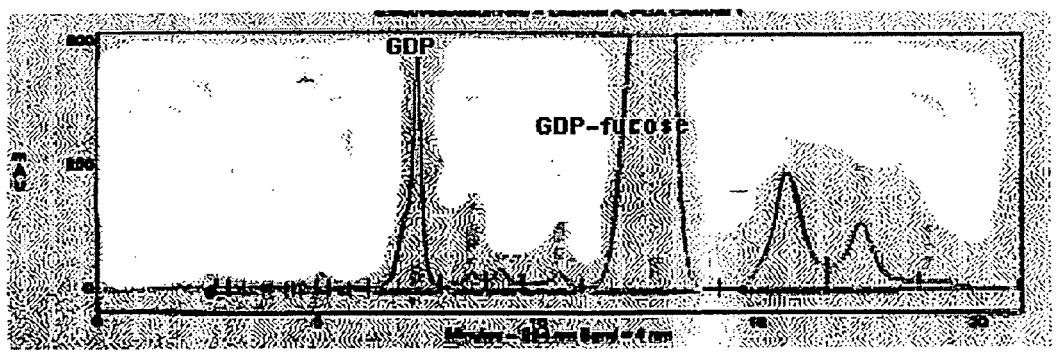
FIG. 9 shows the results of a large-scale conversion of GDP-mannose to GDP-fucose using GMD and YEF B.

In an alternative embodiment, the GDP produced in conjunction with the fucosyltransferase reaction is converted to GTP, which does not inhibit fucosyltransferase or GMD. For example, the reaction mixture can include a kinase and corresponding substrate. Suitable kinases include, for example, polyphosphate kinase (EC 2.7.4.1), nucleoside phosphate kinases (EC 2.7.4.4), creatine kinase (EC 2.7.3.2); myokinase (EC 2.7.4.3); myokinase (EC 2.7.4.3); acetyl kinase (e.g., EC 2.7.1.59); acetyl phosphate kinase; and pyruvate kinase (EC 2.7.1.40). Suitable substrates for these enzymes are known to those of skill in the art. A reaction scheme that incorporates this embodiment is shown in FIG. 9.

Figure 15:
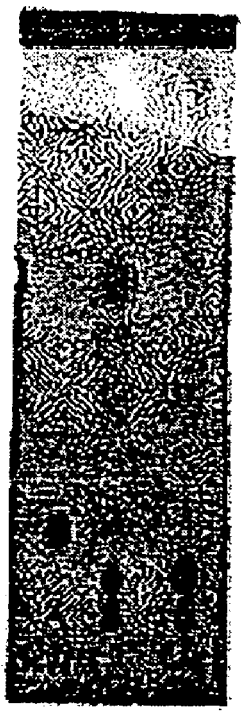
FIG. 15 shows a TLC analysis of the products of a GDP-mannose fucosyltransferase half-cycle reaction. From left to right: Lane 1, SLN; Lane 2, reaction at 2 days; Lane 3, sialyl Lewis X.

In a preferred embodiment, the GDP-fucose synthesizing enzymes are used in an enzymatic cycle. Suitable enzymatic cycles include half-cycles such as is shown in FIG. 15, which uses GDP-mannose as the starting material, and full cycles, such as that shown in FIG. 16, which uses mannose as the starting material. An example of a GDP-mannose half-cycle (FIG. 15) uses glucose dehydrogenase to enzymatically recycle NADPH, a cofactor required by the epimerase/reductase polypeptides, and fucosyltransferase V to transfer fucose to SLN, resulting in formation of a sialyl-Lewis$^x$ compound. Since GDP inhibits both the fucosyltransferase and GDP-mannose dehydratase, a phosphatase that is able to cleave the GDP but does not cleave the phosphate from NADP is preferably added to the cycle. MgCl$_2$ is preferred as a source of divalent cation, as YEF B is inhibited by MnCl$_2$. In addition to GDP-mannose dehydratase and epimerase/reductase polypeptides, the GDP-mannose half-fucosyltransferase cycle preferably includes the following: an enzyme that recycles NADPH, such as glucose dehydrogenase, a substrate for the NADPH regenerating enzyme such as glucose or galactose, fucosyltransferase, an acceptor oligosaccharide or glycoconjugate, NADP, GDP-mannose and a buffer system.

Figure 16:
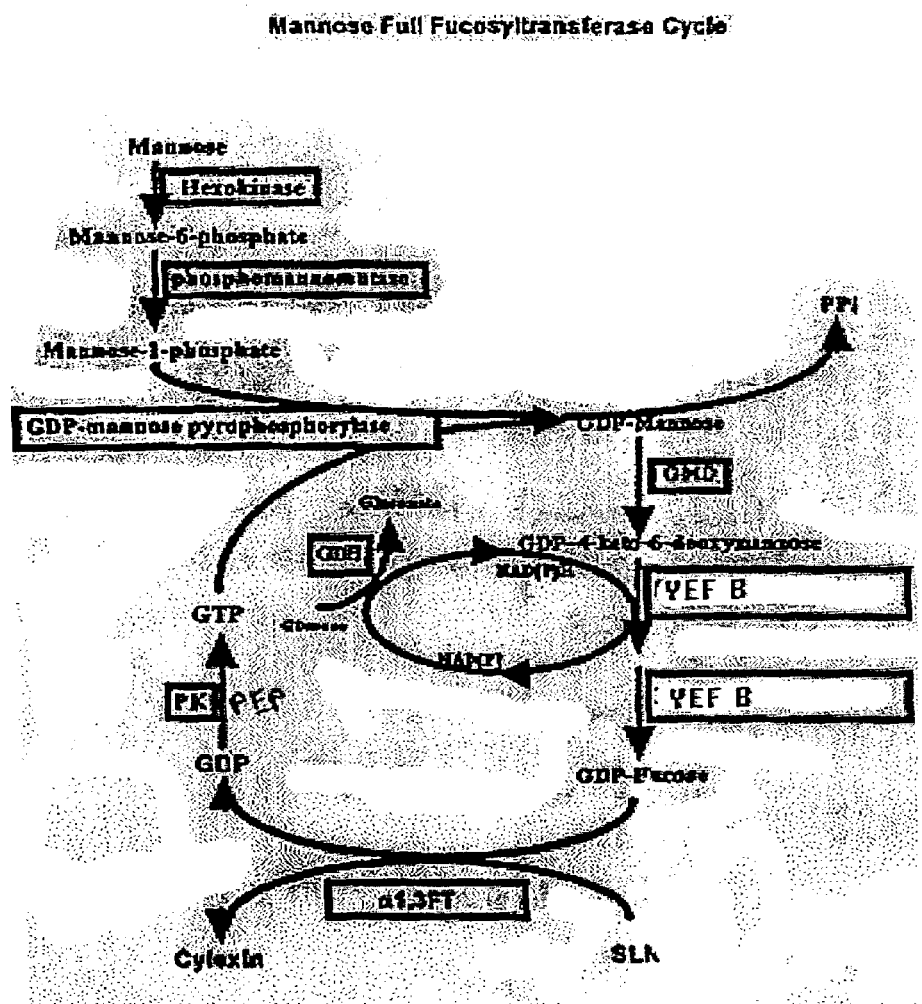
FIG. 16 shows a schematic diagram of a mannose fucosyltransferase full-cycle reaction.

Alternatively, the enzymes can be used in a "mannose full cycle," as shown in FIG. 16. GDP-mannose dehydratase and an epimerase/reductase polypeptide can be used in conjunction with GDP-mannose pyrophosphorylase, GDP-phosphomannomutase, hexokinase and pyruvate kinase in a complete or "full" mannose fucosyltransferase cycle. The full cycle allows one to use simply mannose and the desired acceptor saccharide as the starting material. Either recombinant or naturally occurring enzymes can be used.

The reaction methods of the invention can be optimized by altering the divalent cations present in the reaction mixture, the pH of the reaction, temperature, and additives such as alkaline phosphatase that may improve the reaction kinetics by removal of inhibitory bi-products such as GDP. For example, as discussed above, GDP is known to inhibit both GDP-mannose dehydratase and fucosyltransferase (Broschat et al (1985) *Eur. J. Biochem.* 153: 397-401; Staudacher, E. (1996) *TIGG* 8: 391-408).

Further improvement in the fucosylation reactions can be obtained by supplementing the divalent cations present in the reaction mixture as the reaction proceeds. Glycosyltransferase cycles (See, U.S. Pat. No. 5,374,541 and WO 9425615 A) typically produce one or more moles of inorganic pyrophosphate for each mole of product formed and are typically carried out in the presence of a divalent metal ion. The metal ion is a cofactor for at least one of the enzymes in each of the cycles. However, the divalent metal cations play a dual role in the glycosyltransferase cycles. In particular, the divalent metal ion forms a complex of very low solubility with inorganic phosphate or pyrophosphate produced by various processes in the glycosyltransferase cycles. As a result, the metal ion can remove the Pi or PPi from the reaction by precipitation. This, in turn, results in reduced amounts of metal ions present in solution and a corresponding decrease in the overall turnover rates for those enzymes which require the metal ion cofactors. To circumvent this problem, the methods of the invention can include adding sufficient divalent metal cation to the reaction medium to restore a portion of the divalent cation lost during the course of the reaction to thereby achieve or maintain a concentration of divalent metal cation in the reaction medium between about 1 mM and about 75 mM. Preferably, the addition of divalent metal cation occurs without interruption of said enzymatic conversion. See, e.g., International Patent Application Publ. No. WO96/32491.

Once the reactions of the invention are optimized for the GDP-mannose dehydratase and an epimerase/reductase such as YEF B, other analogs of these enzymatic activities can be tested using a similar process. For example, human Fx can be substituted for YEF B.

TABLE 2

Fucosyltransferases that are useful in fucosyltransferase cycles.

| Fucosyltransferase | Reference |
|---|---|
| α1,3/4Fuc-T III | Kukowska-Latallo et al (1990) Genes Dev. 4: 1288–1303 |
| α1,3Fuc-T IV | Kumar et al (1991) J. Biol. Chem. 266: 21777–21783 |
| α1,3Fuc-T V | Weston et al (1992) J. Biol. Chem. 267: 4152–4160 |
| α1,3Fuc-T VI | Weston et al (1992) J. Biol. Chem. 267: 24575–24584 |
| α1,3Fuc-T VII | Natsuka et al (1994) J. Biol. Chem. 270: 20112–20122 |
| α1,3Fuc-T bacterial | Ge et al (1997) J. Biol. Chem. 272: 21357–21363 |
| α1,2Fuc I | Sarnesto et al (1992) J. Biol. Chem. 267: 2745–2752 |
| α1,2Fuc-T II | Larsen et al (1990) Proc. Nat'l. Acad. Sci. USA 87: 6674–6678 |

For glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants. Preferably, the concentrations of activating nucleotides, phosphate donor, the donor sugar and enzymes are selected such that glycosylation proceeds until the acceptor is consumed, thus completely sialylating the saccharide groups present on the glycoprotein.

Enzyme amounts or concentrations are expressed in activity Units, which is a measure of the initial rate of catalysis. One activity Unit catalyzes the formation of 1 µmol of product per minute at a given temperature (typically 37° C.) and pH value (typically 7.5). Thus, 10 Units of an enzyme is a catalytic amount of that enzyme where 10 µmols of substrate are converted to 10 µmol of product in one minute at a temperature of 37° C. and a pH value of 7.5.

The above ingredients are typically combined by admixture in an aqueous reaction medium (solution). That medium has a pH value of about 6 to about 8.5. The medium is devoid of chelators that bind enzyme cofactors such as $Mg^{+2}$ or $Mn^{+2}$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8.5, preferably about 7.2 to 7.8, by the addition of base. A suitable base is NaOH, preferably 6 M NaOH.

The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C. to about 45° C., or up to 100° C. or more for an enzyme obtained from a thermophylic organism. A typical range for non-thermophilic enzymes is about 20° C. to about 37° C.

The reaction mixture so formed is maintained for a period of time sufficient for the desired percentage of acceptor sugar residues to be fucosylated. For commercial-scale preparations, the reaction will often be allowed to proceed for about 8-240 hours, with a time of between about 24 and 48 hours being more typical.

D. Uses of GDP-Fucose Synthesized Using the Methods of the Invention

The methods of the invention are useful for synthesis of GDP-fucose, which finds use in the synthesis of a wide variety of carbohydrate compounds of interest. The carbohydrate compounds can be oligosaccharide or polysaccharide structures, on glycoproteins, glycolipids, or free molecules.

GDP-fucose produced using the methods of the invention can be used, for example, for the synthesis of a wide variety of fucosylated carbohydrates. In conjunction with appropriate fucosyltransferase enzymes, the following carbohydrate structures are among those that one can obtain using the GDP-fucose: (1) Fucα(1→2)Galβ-; (2) Galβ(1→3)[Fucα(1→4)]GlcNAcβ-; (3) Galβ(1→4)[Fucα(1→3)]GlcNAcβ-; (4) Galβ(1→4)[Fucα(1→3)]Glc; (5)-GlcNAcβ(1→4)[Fucα(1→6)]GlcNAcβ→Asn; (6)-GlcNAcβ(1→4)[Fucα(1→3)]GlcNAcβ→Asn; (7) Fucα(1→6)Galβ→; (8) Fucα(1→3)Galβ-; (9) Glcβ(1→3)Fucα1→O-Thr and Fucα1→O-Thr/Ser; (10) Fucα1→Ceramide; and (11) Fucα(1→3)Fuc. Examples of products that can be formed using GDP-fucose as a reactant include, but are not limited to, those listed in Table 3.

TABLE 3

Oligosaccharide Structures Synthesized using GDP-fucose and Fucosyltransferase

| Oligosaccharide | Tissue source |
| --- | --- |
| III³ Fucosyl-para-lacto-N-hexaose | Human milk |
| 3'-Sialyl-3-fucosyllactose | Human milk |
| Lewis X | hematopoietic cells |
| Lewis A | hematopoietic cells |
| Sialyl lewis X | hematopoietic cells |
| Sialyl lewis A | hematopoietic cells |
| Lacto-N-difucohexaose II | Human milk |
| Lacto-N-fucopentaose I | Human milk |
| Lacto-N-fucopentaose II | Human milk |
| 2'-Fucosyllactose | Human milk |
| Lactodifucotetraose | Human milk |
| 3-Fucosyllactose | Human milk |
| Lacto-N-fucopentaose III | Human milk |
| Lacto-N-difucohexaose I | Human milk |
| Lacto-N-fucopentaose V | Human milk |

For example, the present invention provides recombinant cells and methods for the preparation of compounds having the formula Galβ(1→4)(Fucα1→3)GlcN(R')β-R and Galβ(1→3)(Fucα1→4)GlcN(R')β-R. In these embodiments, the acceptor saccharide is either Galβ(1→4)GlcN(R')β-R or Galβ(1→3)GlcN(R')β-R, respectively, wherein R is selected from the group consisting of hydrogen, a saccharide, an oligosaccharide and an a glycon group having at least one carbon atom; and R' is selected from the group consisting of acetyl and allyloxycarbonyl.

Suitable acceptor saccharides include, for example, NeuAcα(2→3)Gal β(1→4)GlcN(R')β(1→3)Galβ-OR and NeuAcα(2→3)Galβ(1→3)GlcN(R')β(1→3)Galβ-OR.
These acceptor saccharides can be formed by sialylating a compound Galβ(1→4)GlcN(R') β(1→3)Galβ-OR or Galβ(1→3)GlcN(R')β(1→3)Galβ-OR with a sialyltransferase in the presence of a CMP derivative of a sialic acid using a α(2,3)sialyltransferase under conditions wherein sialic acid is transferred to the non-reducing sugar of the compound. The compounds Galβ(1→4)GlcN(R')β(1→3)Galβ-OR and Galβ(1→3)GlcN(R')β(1→3)Galβ-OR can be formed by galactosylating a compound of the formula GlcN(R')β(1→3)Galβ-OR or GlcN(R')β(1→3)Galβ-OR, respectively, with a galactosyltransferase in the presence of a UDP-galactose under conditions sufficient to form the compound.

In some embodiments of the invention, methods are provided for synthesizing NeuAcα(2→3)Galβ(1→4)(Fucα1→3)GlcN(R')β(1→3)Galβ-OR or NeuAcα(2→3)Gal β(1→3)(Fucα1→4)GlcN(R')β(1→3)Galβ-OR. In these formulae, R is a hydrogen, a saccharide, an oligosaccharide or an aglycon group having at least one carbon atom. R' can be either acetyl or allyloxycarbonyl (Alloc). The term "aglycon group having at least one carbon atom" refers to a group -A-Z, in which A represents an alkylene group of from 1 to 18 carbon atoms optionally substituted with halogen, thiol, hydroxy, oxygen, sulfur, amino, imino, or alkoxy; and Z is hydrogen, —OH, —SH, —NH$_2$, —NHR$^1$, —N(R$^1$)$_2$, —CO$_2$H, —CO$_2$R$^1$, —CONH$_2$, —CONHR$^1$, —CON(R$^1$)$_2$, —CONHNH$_2$, or —OR$^1$ wherein each R$^1$ is independently alkyl of from 1 to 5 carbon atoms. In addition, R can be

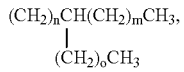

where n,m,o=1-18; (CH$_2$)$_n$—R$^2$ (in which n=0-18), wherein R$^2$ is a variously substituted aromatic ring, preferably, a phenyl group, being substituted with one or more alkoxy groups, preferably methoxy or O(CH$_2$)$_m$CH$_3$, (in which m=0-18), or a combination thereof.

The steps involved in synthesizing these compounds include:

(a) galactosylating a compound of the formula GlcNR'β(1→3)Galβ-OR with a galactosyltransferase in the presence of a UDP-galactose under conditions sufficient to form the compound: Galβ(1→4)GlcNR'β(1→3)Galβ-OR;

(b) sialylating the compound formed in (a) with a sialyltransferase in the presence of a CMP derivative of a sialic acid using a α(2,3)sialyltransferase under conditions in which sialic acid is transferred to the non-reducing sugar to form the compound: NeuAcα(2→3)Galβ(1→4)GlcNR'β(1→3)Galβ-OR; and (c) fucosylating the compound formed in (b) to provide the NeuAcα(2→3)Galβ(1→4)(Fucα1→3)GlcNR'β(1→3)Galβ-OR.

The fucosylating step is preferably carried out using the methods of the invention, as described above. In a presently preferred embodiment, at least two of the reaction steps are carried out using recombinant cells of the invention. The different glycosyltransferases can be expressed by the same cell, or different recombinant cells which each contain an exogenous glycosyltransferase gene and can be mixed together. Thus, by mixing and matching members of a set of recombinant cells, each of which contain a different glycosyltransferase, one can readily create a custom reaction mixture for performing many multi-step glycosylation reactions.

In yet another aspect, the present invention provides methods for the preparation of compounds as described in WO 94/26760. Generally these compounds have the formula:

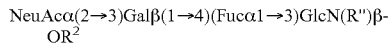

In this formula, R" is alkyl or acyl from 1-18 carbons, 5,6,7,8-tetrahydro-2-naphthamido; benzamido; 2-naphthamido; 4-amino benzamido; or 4-nitrobenzamido. R$^2$ may be the same as R as described above or may be Galβ-OR (R is as described above).

In the above descriptions, the terms are generally used according to their standard meanings. The term "alkyl" as used herein means a branched or unbranched, saturated or unsaturated, monovalent or divalent, hydrocarbon radical having from 1 to 20 carbons, including lower alkyls of 1-8 carbons such as methyl, ethyl, n-propyl, butyl, n-hexyl, and the like, cycloalkyls (3-7 carbons), cycloalkylmethyls (4-8 carbons), and arylalkyls.

The term "aryl" refers to a radical derived from an aromatic hydrocarbon by the removal of one atom, e.g., phenyl from benzene. The aromatic hydrocarbon may have more than one unsaturated carbon ring, e.g., naphthyl. The term "alkoxy" refers to alkyl radicals attached to the remainder of the molecule by an oxygen, e.g., ethoxy, methoxy, or n-propoxy. The term "alkylthio" refers to alkyl radicals attached to the remainder of the molecule by a sulfur.

The term of "acyl" refers to a radical derived from an organic acid by the removal of the hydroxyl group. Examples include acetyl, propionyl, oleoyl, myristoyl.

The present invention is also useful for synthesizing a variety of compounds that comprise selectin-binding carbohydrate moieties. These selectin-binding moieties have the general formula:

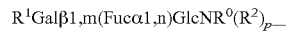

in which R$^0$ is (C$_1$-C$_8$ alkyl)carbonyl, (C$_1$-C$_8$ alkoxy)carbonyl, or (C$_2$-C$_9$ alkenyloxy)carbonyl, R$^1$ is an oligosaccharide or a group having the formula

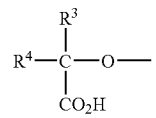

R$^3$ and R$^4$ may be the same or different and may be H, C$_1$-C$_8$ alkyl, hydroxy-(C$_1$-C$_8$ alkyl), aryl-(C$_1$-C$_8$ alkyl), or (C$_1$-C$_8$ alkoxy)-(C$_1$-C$_8$ alkyl), substituted or unsubstituted. R$^2$ may be H, C$_1$-C$_8$ alkyl, hydroxy-(C$_1$-C$_8$ alkyl), aryl-(C$_1$-C$_8$-alkyl), (C$_1$-C$_8$ alkyl)-aryl, alkylthio, α1,2Man, α1,6GalNAc, β1,3Galβ1,4Glc, α1,2Man-R$^8$, α1,6GalNAc-R$^8$, and β1,3Gal-R$^8$. R$^8$ may be H, C$_1$-C$_8$ alkyl, C$_1$-C$_8$ alkoxy, hydroxy-(C$_1$-C$_8$ alkyl), aryl-(C$_1$-C$_8$ alkyl), (C$_1$-C$_8$ alkyl)-aryl, or alkylthio. In the formula, m and n are integers and may be either 3 or 4; p may be zero or 1.

The substituted groups mentioned above may be substituted by hydroxy, hydroxy(C$_1$-C$_4$ alkyl), polyhydroxy(C$_1$-C$_4$ alkyl), alkanoamido, or hydroxyalknoamido substituents. Preferred substituents include hydroxy, polyhydroxy(C$_3$ alkyl), acetamido and hydroxyacetamido. A substituted radical may have more than one substitution, which may be the same or different.

For embodiments in which R$^1$ is an oligosaccharide, the oligosaccharide is preferably a trisaccharide. Preferred trisaccharides include NeuAcα2,3Galβ1,4GlcNAcβ1,3 or NeuGcα2,3Galβ1,4GlcNAcβ1,3.

For embodiments in which R$^1$ is the group having the formula:

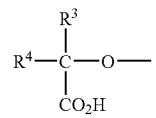

R$^3$ and R$^4$ preferably form a single radical having the formula:

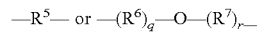

in which R$^5$ is C$_3$-C$_7$ divalent alkyl, substituted or unsubstituted, R$^6$ and R$^7$ are the same or different and are C$_1$-C$_6$ divalent alkyl, substituted or unsubstituted. In the formula, q and r are integers which may be the same or different and are either zero or 1. The sum of q and r is always at least 1.

A more preferred structure for a single radical formed by R$^3$ and R$^4$ is one having the formula:

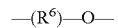

in which $R^6$ is $C_3$-$C_4$ divalent alkyl, substituted or unsubstituted. For instance, $R^6$ may have the formula —$CH_2$—$CH_2$—$H_2$—$CH_2$—, preferably substituted. The radical can be substituted with hydroxy, polyhydroxy($C_3$ alkyl), and substituted or unsubstituted alkanoamido groups, such as acetamido or hydroxyacetamido. The substituted structure will typically form a monosaccharide, preferably a sialic acid such as NeuAc or NeuGc linked α2,3 to the Gal residue.

In the general formula, above, both m and n are integers and can be either 3 or 4. Thus, in one set of structures Gal is linked β1,4 and Fuc is linked α1,3 to GlcNAc. This formula includes the SLe$^x$ tetrasaccharide. SLe$^x$ has the formula NeuAcα2,3Galβ1,4(Fucα1,3)GlcNAcβ1-. This structure is selectively recognized by LECCAM-bearing cells. SLe$^x$ compounds that can be purified using the methods of the invention include NeuAcα2,3Galβ1,4(Fucα1,3)GlcNAcβ1-Gal-OEt, NeuAcα2,3Galβ1,4(Fucα1,3)GlcNAcβ1,4Galβ1-OEt, and others that are described in international application WO 91/19502. Other compounds that one can purify using the methods include those described in U.S. Pat. No. 5,604,207 having the formula

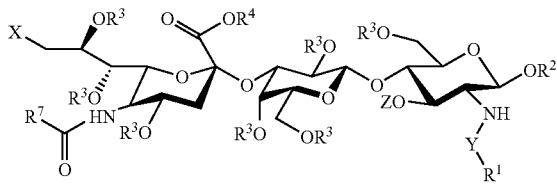

wherein Z is hydrogen, $C_1$-$C_6$ acyl or

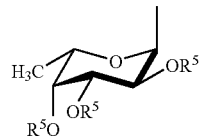

Y is selected from the group consisting of C(O), $SO_2$, HNC(O), OC(O) and SC(O);

$R^1$ is selected from the group consisting of an aryl, a substituted aryl and a phenyl $C_1$-$C_3$ alkylene group, wherein said aryl substitutent is selected from the group consisting of a halo, trifuloromethyl, nitro, $C_1$-$C_{18}$ alkyl, $C_1$-$C_{18}$ alkoxy, amino, mono-$C_1$-$C_{18}$ alkylamino, di-$C_1$-$C_{18}$ alkylamino, benzylamino, $C_1$-$C_{18}$ alkylbenzylamino, $C_1$-$C_{18}$ thioaklyl and $C_1$-$C_{18}$ alkyl carboxamido groups, or $R^1Y$ is allyloxycarbonyl or chloroacetyl;

$R^2$ is selected from the group consisting of monosaccharide (including β1,3Gal-OR, where R═H, alkyl, aryl or acyl), disaccharide, hydrogen, $C_1$-$C_{18}$ straight chain, branched chain or cyclic hydrocarbyl, $C_1$-$C_6$ alkyl, 3-(3,4,5-trimethoxyphenyl)propyl, $C_1$-$C_5$ alkylene ω-carboxylate, ω-trisubstituted silyl $C_2$-$C_4$ alkylene wherein said (o-trisubstituted silyl is a silyl group having three substituents independently selected from the group consisting of $C_1$-$C_4$ alkyl, phenyl, or $OR^2$ together form a $C_1$-$C_{18}$ straight chain, branched chain or cyclic hydrocarbyl carbamate;

$R^3$ is hydrogen or $C_1$-$C_6$ acyl;

$R^4$ is hydrogen, $C_1$-$C_6$ alkyl or benzyl;

$R^5$ is selected from the group consisting of hydrogen, benzyl, methoxybenzyl, dimethoxybenzyl and $C_1$-$C_6$ acyl;

$R^7$ is methyl or hydroxymethyl; and

X is selected from the group consisting of $C_1$-$C_6$ acyloxy, $C_2$-$C_6$ hydroxylacyloxy, hydroxy, halo and azido.

A related set of structures included in the general formula are those in which Gal is linked β1,3 and Fuc is linked α1,4. For instance, the tetrasaccharide, NeuAcα2,3Galβ1,3(Fucα1,4)GlcNAcβ1-, termed here SLe$^a$, is recognized by selectin receptors. See, Berg et al., *J. Biol. Chem*, 266: 14869-14872 (1991). In particular, Berg et al. showed that cells transformed with E-selectin cDNA selectively bound neoglycoproteins comprising SLe$^a$.

The GDP-fucose produced by the methods of the invention can be used to modify oligosaccharides present on glycoconjugates, including glycoproteins and glycolipids. Proteins that can be modified by the methods of the invention include, for example, hormones such as insulin, growth hormones (including human growth hormone and bovine growth hormone), tissue-type plasminogen activator (t-PA), renin, clotting factors such as factor VIII and factor IX, bombesin, thrombin, hemopoietic growth factor, serum albumin, receptors for hormones or growth factors, interleukins, colony stimulating factors, T-cell receptors, MHC polypeptides, viral antigens, glycosyltransferases, and the like: Polypeptides of interest for recombinant expression and subsequent modification using the methods of the invention also include α1-antitrypsin, erythropoietin, granulocyte-macrophage colony stimulating factor, anti-thrombin III, interleukin 6, interferon β, protein C, fibrinogen, among many others. This list of polypeptides is exemplary, not exclusive. The methods are also useful for modifying the glycosylation patterns of chimeric proteins, including, but not limited to, chimeric proteins that include a moiety derived from an immunoglobulin, such as IgG.

The following examples are offered to illustrate, but not to limit the present invention.

EXAMPLE 1

Cloning and Expression of Nucleic Acids Encoding GDP-Fucose Synthesizing Enzymes This Example describes the cloning and expression of nucleic acids that encode enzymes useful in the enzymatic conversion of GDP-mannose to GDP-fucose, and the use of these enzymes to produce GDP-fucose.

Methods

A. Amplification of GDP-Mannose 4,6-Dehydratase Open Reading Frame

The GDP-mannose dehydratase (GMD) open reading frame was amplified by PCR using primers based on the known sequence for GMD (Stevenson et al. (1996) *J. Bacteriol.* 178: 4885-4893; Tonetti et al. (1996) *J. Biol. Chem.* 271: 27274-27279). Genomic DNA from *E. coli* K12 was purified using a kit from Qiagen, Inc. following the manufacturer's directions. To amplify the GMD open reading frame, the following primers were utilized: 5' primer: 5'-CGCTCTAGATACATGTCAAAAGTCGCT-3' (SEQ ID NO: 2); 3' primer: 5'-GCGAAGCTTTTATGACTC-CAGCGCGAT-3' (SEQ ID NO: 3). The open reading frame for GDP-mannose dehydratase corresponds to nucleotides 8633-9754 of the wca gene cluster of *E. coli* K12 (Stevenson et al., supra.) (8659-9780 in GenBank Accession No. U38473). Each primer was designed with a 5' XbaI site and a 3' HindIII site. 100 pmole of each primer pair was combined with genomic DNA from *E. coli* K12. Thirty cycles (95° C. for 45 sec, 65° C. for 1 min, 73° C. for 3 min)

were run using Pfu polymerase. The products were gel purified, digested with XbaI and HindIII and subcloned into these sites of the bacterial expression plasmid pTGK (PCT/US97/20528; Int'l. Publ. No. WO 9820111). Sequencing of the plasmid revealed authentic GDP-mannose dehydratase with an ATG start site positioned appropriately for expression in pTGK. This resulted in the expression plasmid pTGK:GDP-mannose dehydratase (pTGK:GMD).

B. Expression of GDP-Mannose Dehydratase E. coli JM101

After transformation of pTGK:GMD into the E. coli strain JM101 using standard molecular biology protocols, isolated colonies were grown in M9 defined media containing galactose to induce the expression of the open reading frame. After an overnight incubation at 37° C. with shaking, cells were pelleted and resuspended in 50 mM Tris pH 8.0 on ice (5 times the pellet volume). The cells were lysed at 4° C. with a French press. The cellular debris and unlysed cells were pelleted in a centrifuge (3000 rpm; Beckman floortop centrifuge) for 10 minutes. The resulting supernatant was stored on ice until analysis, up to 2 hours, by SDS-PAGE and activity assay.

C. Assay of GDP-Mannose Dehydratase

To assay GDP-mannose dehydratase activity, a reverse phase HPLC assay was developed. An Aquasil C18 reverse phase column was set up in line on a Beckman 126 solvent monitor. The column was eluted isocratically with 0.5M $KH_2PO_4$ over twenty minutes with a flow rate of 1 ml/min. A photodiode array detector was employed to monitor the elution scanning the 210-300 nm wavelength range. GDP-mannose dehydratase activity was determined by reacting GDP-mannose dehydratase extract with 480 nmole of GDP-mannose in 50 mM Tris pH 7.5, 0.15 mM $NADP^+$ ($NADP^+$ is absolutely required for GDP-mannose dehydratase activity) in a 100 µl reaction volume. Twenty µl of the assay mix was injected over the C18 column.

By comparing the peak area of the no enzyme control, corresponding to 200 nmole, the decrease in the peak area of GDP-mannose was used to directly measure the activity of GDP-mannose dehydratase by the following formulae:

(No enzyme peak area)−(enzyme peak area)=(Peak area of GDP-mannose consumed)    1.

(Peak area of GDP-mannose consumed)/(No enzyme peak area)=% of 200 nmole GDP-mannose consumed.    2.

To control for any carryover loss upon HPLC injection, 10 nmole of CTP was added to the sample to be analyzed.

D. Amplification of YEF B, Human Fx and wca H Open Reading Frames

Nucleic acids that include the open reading frames of YEF·B, wcaH, and human Fx were amplified using primers that were synthesized based on the reported nucleotide sequences (Stevenson et al. (1996) supra.; Tonetti et al. (1996) supra.). Genomic DNA from E. coli K12 was purified using a kit from Qiagen, Inc. following the manufacturer's directions. To amplify these open reading frames the following primers were utilized:

YEF B

```
                                          (SEQ ID NO: 4)
5' primer:
5'-CGTCCTAGAGCGATGAGTAAACAACGAGTT-3';

3' primer:
5'-GCGAAGCTTTTACCCCCGAAAGCGGTC-3';    (SEQ ID NO: 5)
``` wca H

```
                                          (SEQ ID NO: 6)
5' primer:   5'-GCTCTAGAGTAATGATGTTTTTACGTCAGG-3';

(SEQ ID NO: 7)
3' primer    5'-CCCAAGCTTTCATAATCCGGGTACTCCGGT-3';
and
```

Human Fx

```
                                          (SEQ ID NO: 8)
5' primer:   5'-GCTCTAGAGACATGGGTGAACCCCAGGGAT-3';

(SEQ ID NO: 9)
3' primer:   5'-ACGAAGCTTCACTTCCGGGCCTGCTCGTAGTTG-3'.
```

YEF B and wcaH correspond to nucleotides 9757-10722 (9783-10748 in GenBank Accession No. U38473) and 10722-11204 (10748-11230 in GenBank Accession No. U38473), respectively, of the wca gene cluster of E. coli K12 (Stevenson et al., supra.).

Each primer was designed with a 5' XbaI site and a 3' HindIII site. One hundred pmole of each primer pair was combined with genomic DNA from E. coli K12 or, in the case of human Fx, cDNA from human placenta. Thirty cycles (95° C. for 45 sec, 65° C. for 1 min, 73° C. for 3 min) were run with Pfu polymerase. The products were gel purified, digested with XbaI and HindIII and subcloned into these sites of the bacterial expression plasmid pTGK (PCT/US97/20528; Int'l. Publ. No. WO 9820111). This resulted in the following expression plasmids: pTGK:YEF B, pTGK:human Fx (pTGK:Fx) and pTGK:wcaH.

E. Expression of YEF B (wcaG), Human Fx and wcaH in E. coli JM101

After transformation of pTGK:YEF B, pTGK:Fx and pTGK:wcaH into the E. coli strain JM101 using standard molecular biology protocols, isolated colonies were grown in M9 defined media containing galactose to induce the expression of the open reading flames. After an overnight incubation at 37° C. with shaking, cells were pelleted and resuspended in 50 mM Tris pH 8.0 on ice (5 times the pellet volume). The cells were lysed at 4° C. with a French press. The cellular debris and unlysed cells were pelleted in a centrifuge (3000 rpm Beckman floortop) for 10 minutes. The resulting supernatant was stored on ice until analysis, up to 2 hours, by SDS-PAGE and activity assay.

F. Activity Assay for YEF B and Human Fx

To assay YEF B activity, a reverse phase HPLC assay was developed. An Aquesil C18 reverse phase column was set up in-line on a Beckman 126 solvent monitor. The column was eluted isocratically with 0.5M $KH_2PO_4$ over twenty minutes with a flow rate of 1 ml/min. A photodiode array detector was employed to monitor the elution scanning the 210-300 nm wavelength range.

A coupled assay was employed to assay YEF B activity. This was required since its substrate, GDP-4-keto-6-deoxymannose, is unstable and not commercially available. Twenty mUnit of GDP-mannose dehydratase was allowed to react with 480 nMole of GDP-mannose for 20 minutes under standard assay conditions as previously. At this time greater than 90% of the GDP-mannose has been converted to GDP-4-keto-6-deoxymannose, the substrate for YEF B. The following additions were then made: 500 nmole glucose, MgCl$_2$ to 20 mM, NADPH to 0.15 mM, 10 mUnit glucose dehydrogenase, 100 nmole CTP (to normalize for losses that may occur when sample is injected onto HPLC), YEF B and water to 50 μl. The reaction was allowed to proceed for ten minutes at which point the reaction was stopped by freezing on dry ice. After thawing 10 μl aliquots were analyzed by reverse phase HPLC analysis. The amount of GDP fucose formed was calculated by analyzing a separate assay mix in the absence of GDP-mannose dehydratase to yield a 100% value for the absorption peak of GDP-mannose. This peak area was then divided by the peak area of GDP-fucose formed to yield percentage of GDP-fucose formed. (% GDP-fucose)(nMole GDP-mannose in reaction)=nMole GDP-fucose formed.

G. Characterization of the Sugar Nucleotide Formed by GDP-Mannose Dehydratase and YEF B To confirm that GDP-mannose dehydratase and YEF B convert GDP-mannose into GDP-fucose, GDP-mannose dehydratase and YEF B extracts were reacted with 5 mg of GDP-mannose and 6 mg of NADPH in 50 mM Tris pH 8.0. The reaction volume was 1 ml. After 3 hours, 95% of the GDP-mannose was converted into an adsorption peak that migrated with GDP-fucose. The reaction was quenched with 2 ml methanol, the precipitate was pelleted and the supernatant was dried under vacuum. The resulting sugar nucleotide was then reacted with sialyl N-acetyllactosamine (SLN; a precursor to sialyl Lewis$^x$), fucosyltransferase V (20 mUnit), 1 mM MnCl$_2$ in 50 mM Tris pH 7.5 for 24 hours at 37° C. The reaction volume was 200 μl. The reaction was approximately 80-85% complete as judged by TLC. The oligosaccharide product was resolved from nucleotides and protein by purification over a 15 ml P2 column eluted with 20% ethanol and monitoring the elution with a photodiode array detector. The oligosaccharide product was then dried under vacuum, protons exchanged with D$_2$O and subjected to 500 Mhz proton NMR. This analysis revealed that authentic sialyl Lewis$^x$-containing compound was formed, demonstrating that GDP-mannose dehydratase and YEF B act in concert to form GDP-fucose.

H. Synthesis of GDP-Fucose at 0.2 kG Scale 800 grams of a bacterial cell pellet expressing GDP-mannose dehydratase (GMD) was resuspended in 4 liters of ice cold 50 mM Tris pH 7.5. The cells were disrupted by one passage through a microfluidizer, debris was pelleted by centrifugation at 4,000 rpm for 15 minutes and the supernatant was separated from the pellet by decanting.

200 grams of GDP-mannose, 87% pure by HPLC, was obtained from Boehringer Mannheim and dissolved in 1 liter of 50 mM Tris pH 7.5. To this solution, 4 liters of the GMD extract (2000 Unit) was added along with NADP$^+$ to a final concentration of 0.15 mM. The final concentration of GDP-mannose was 66 mM. Sodium azide was added to 0.05% to inhibit bacterial growth. The reaction was incubated at 32° C. with mild shaking and the reaction followed by HPLC. After 5 hours, 98% of the GDP-mannose had been converted into its intermediate, GDP-4-keto-6-deoxymannose, at which time a YEF B supernatant from a 300 gram bacterial cell pellet expressing YEF B derived identically to GMD supernatant (1500 Unit), was added to the reaction mixture along with 20 mg NADPH, 0.66 mole of glucose (2 molar equivalents to GDP-mannose), and 1800 Unit glucose dehydrogenase. Incubation at 32° C. was continued overnight with mild continuous shaking. The following morning, 100% of the intermediate, GDP-4-keto-6-deoxymannose, had been converted to GDP-fucose as determined by HPLC. This material was passed through a 10 kD MWC tangential flow membrane to remove high molecular weight material including protein and bacterial polysaccharides. The effluent containing GDP-fucose was then precipitated by addition of ethanol to 80%. After storage at 4° C., the supernatant was decanted and the precipitated GDP-fucose was pelleted in a centrifuge at 4500 rpm for 20 minutes. The supernatant was removed and the pellets resuspended in water and lyophilized. From 200 grams of GDP-mannose, 140 grams of GDP-fucose was obtained for a molar yield of 72%. The purity of the GDP-fucose was similar to that of GDP-mannose, approximately 87%.

I. Synthesis of Sialyl Lewis X Antigen at the 100 Gram Scale Using Enzymatic Fucosylation Approximately 128 grams or 0.15 mole of SLN (the tetrasaccharide precursor of sialyl Lewis X) was added to 110 grams or 0.18 mole of GDP-fucose and resuspended in 2.5 liters of water. 5 m Tris pH 7.5 was added to a final concentration of 50 mM and MgCl$_2$ was added to a final concentration of 20 mM. 440 ml of fucosyltransferase V (FT V) at 1.24 Unit/ml purified from *A. niger* broth was added along with 600 units of alkaline phosphatase from Boehringer Mannheim. Sodium azide was added to 0.04%. The final volume was 3 liters. The reaction was monitored by TLC, HPLC to determine the level of GDP-fucose, GDP and MgCl$_2$. The pH of the reaction was monitored by pH meter. The solvent system used for TLC analysis was isopropanol:water 4:1. After the reaction was judged to be complete by TLC, sialyl Lewis X was purified using ultrafiltration.

J. Synthesis of Sialyl Lewis X Antigen at 1 mg Scale Using an Enzymatic Half Cycle The half cycle was run using the following conditions (all concentrations are final): SLN 5 mM; GDP-mannose, 10 mM; Glucose, 18 mM; MgCl$_2$, 20 mM; Tris pH 7.5, 50 mM; NADP$^+$, 0.12 mM; GDP-mannose dehydratase, 1.16 Unit/ml; YEF B 740 mUnit/ml; glucose dehydrogenase, 330 mUnit/ml; FT V, 46 mUnit/ml; pyruvate kinase, 16.5 Unit/ml; sodium azide, 0.04%. The final volume was 220 μl. The reaction was monitored by TLC and HPLC.

Results

A. Characterization of GDP-Mannose Dehydratase

1. Expression of GDP-Mannose Dehydratase

Figure 2:
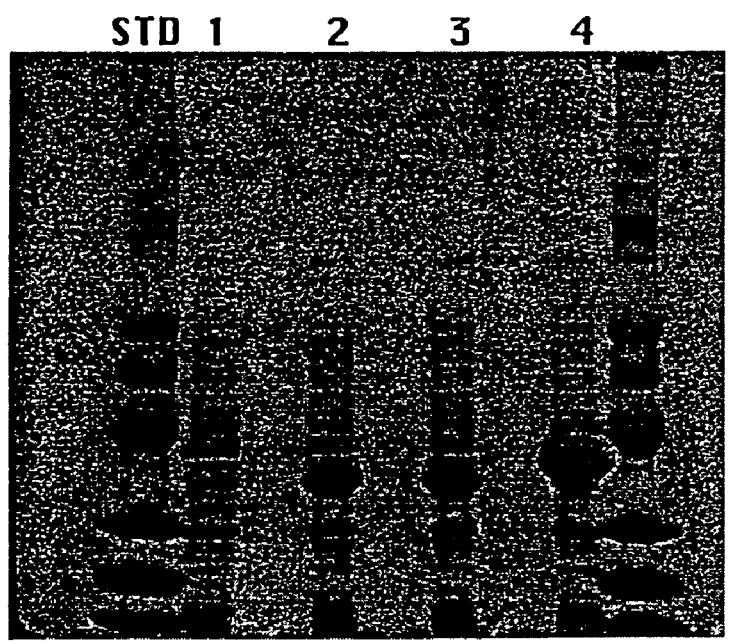
FIG. 2 shows an 8-15% SDS-polyacrylamide gel analysis of extracts from bacterial cells that harbor expression plasmids for enzymes involved in synthesis of GDP-fucose. Molecular weight standards are in the two outside lanes. Extracts are from cells containing the expression vectors pTGK, pTGK:YEF B, pTGK:wcaH, and pTGK:GMD. SDS-PAGE under reducing conditions. Lane 1, pTGK lysate; Lane 2, pTGK:YEF B1 lysate; Lane 3, pTGK:YEF B2 lysate; Lane 4, pTGK:GMD lysate.

The expression of GDP-mannose dehydratase was analyzed by SDS-PAGE. The results are shown in FIG. 2, lane 4. A large band is present at 42 kD, the predicted molecular weight; this band is not present in the vector alone control (lane 1) or the cells expressing YEF B (lanes 2 and 3).

2. Characterization of GDP-Mannose Dehydratase

Figure 3:
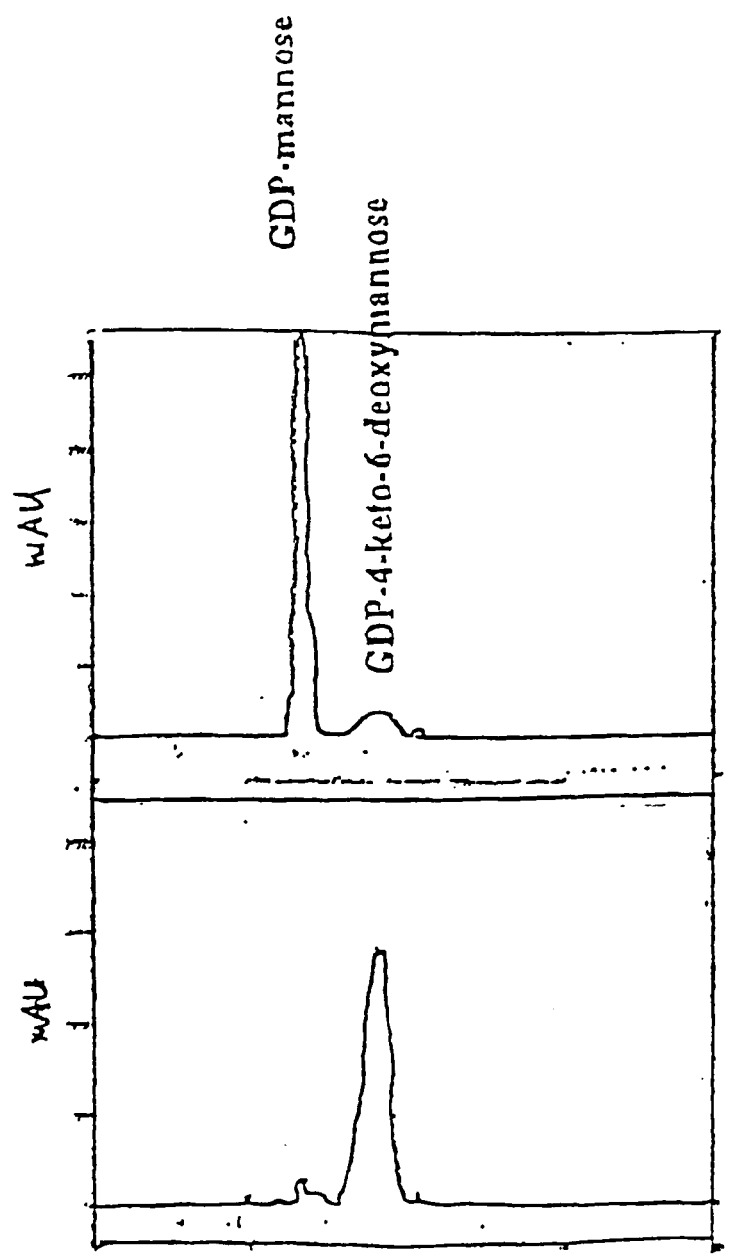
FIG. 3 shows HPLC profiles of the reaction products obtained using the GDP-mannose dehydratase expressed from the expression vector pTGK:GMD.

To characterize the enzymatic activity of GDP-mannose dehydratase, a linear HPLC assay was developed. The assay, which is based on hydrophobic differences between GDP-mannose, GDP-4-keto-6-deoxymannose and GDP-fucose, is capable of resolving GDP-mannose, GDP-4-keto-6-deoxymannose, GDP-4 keto-6-deoxy-galactose and GDP-fucose. Relevant chromatograms are displayed in FIG. 3. The top chromatogram displays GDP-mannose after one minute in the presence of GDP-mannose dehydratase, and the bottom chromatogram displays the same reaction after 55 minutes. As indicated by the chromatograms, greater than 98% of the GDP-mannose has been converted to GDP-4-keto-6-deoxymannose. Proof that this product is GDP-4-keto-6-deoxymannose is demonstrated by addition of NADPH and YEF B or Fx protein converting the product to GDP fucose. The salient features of this assay are: 1) concomitant with a decrease in GDP-mannose there is an increase in the intermediates formed by GDP-mannose 4,6 dehydratase that are resolved by the column, serving as an internal control to demonstrate that the decrease in GDP-mannose is not due to a hydrolytic activity, and 2) quantitative reproducibility.

3. Linearity of the GDP-Mannose Dehydratase Assay with Time

Figure 4:
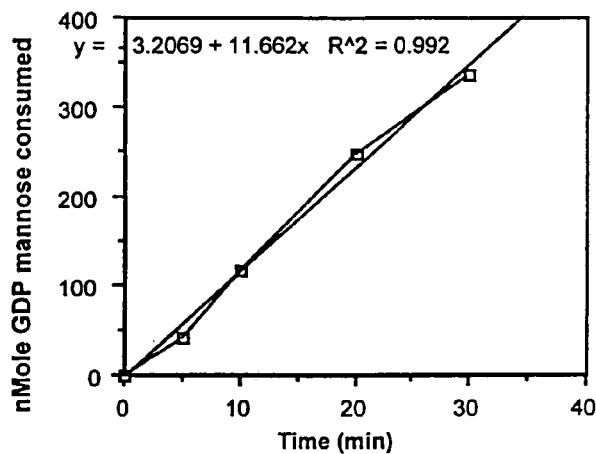
FIG. 4 shows the results of an assay designed to test whether the activity of GMD is linear over time.

To demonstrate the linearity of the GDP-mannose dehydratase assay with time, the standard assay was performed in a single eppendorf tube and 10 µl aliquots were removed at times ranging from 0-30 minutes and immediately frozen on dry ice prior to reverse phase HPLC analysis. Samples were thawed and immediately injected over an aquasil reverse phase HPLC column. As displayed in FIG. 4, the assay is linear up to 30 minutes. Surprisingly, the assay remained linear even when up to 90% of the substrate was consumed. This indicates that the GDP-mannose concentration remains above the Km of GDP-mannose dehydratase and that GDP-4-keto-6 deoxymannose does not inhibit the enzyme.

4. pH Optimum

To determine the pH optimum of the enzyme, pH was varied from pH 6.5-8.0 using 50 mM MES or Tris as buffers and the standard assay performed. Table 4 displays the pH profile of GDP-mannose dehydratase and illustrates a pH optimum of 7.0. Below pH 7.0, the activity is about 70% that of pH 7.0, while pH's above 7.0 yields only a moderate decrease in activity.

TABLE 4 pH Profile of GMD

| pH | Activity (Unit/ml) |
|---|---|
| 6.5 | 3.1 |
| 7.0 | 4.7 |
| 7.5 | 4.5 |
| 8.0 | 4.0 |

Since GDP-mannose dehydratase will be used in conjunction with the epimerase/reductase and fucosyltransferase which both have pH optima of 7.5, pH 7.5 was chosen as the working pH for the standard assay.

5. Dependence on NADP

When assayed in the absence of $NADP^+$, GDP-mannose dehydratase is completely inactive. Additionally, $NAD^+$ will not substitute for $NADP^+$. Moreover, if alkaline phosphatase is included in the assay, GDP-mannose dehydratase activity is severely attenuated. This data is displayed in Table 5 below.

TABLE 5

$NADP^+$ Dependence of GMD

| [NADP] | % GDP-mannose dehydratase activity |
|---|---|
| 0.15 mM | 100 |
| 1 mM | 100 |
| None | not detected |
| 10 mUnit Alkaline Phosphatase | not detected |
| 1 mM NAD | not detected |

6. GDP-Mannose Dehydratase is Not Dependent on Divalent Cations

When GDP-mannose dehydratase was assayed under standard assay conditions in the presence or absence of $MgCl_2$ or $MnCl_2$ at concentrations ranging from 1-20 mM, essentially no effect was observed on activity. These results are illustrated in Table 6.

TABLE 6

Dependence of GMD on Divalent Metal Cations

| [Metal Ion] | % GDP-mannose Dehydratase Activity mUnit/ml |
|---|---|
| 1 mM $MnCl_2$ | 580 |
| 10 mM $MnCl_2$ | 570 |
| 20 mM $MnCl_2$ | 620 |
| 1 mM $MgCl_2$ | 560 |
| 10 mM $MgCl_2$ | 610 |
| 20 mM $MgCl_2$ | 590 |

7. Inhibition of GDP-Mannose Dehydratase by GDP-Fucose

Figure 5:
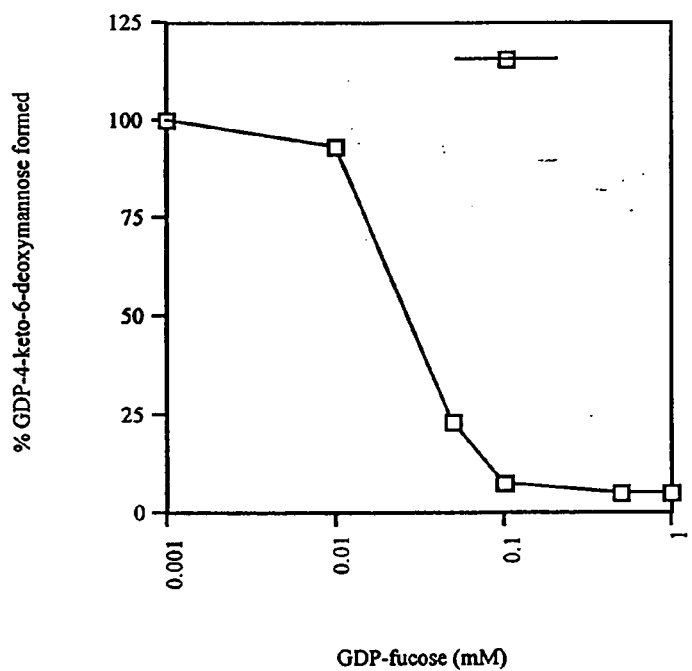
FIG. 5 shows that GDP-fucose is a potent inhibitor of GMD.

Since GDP-mannose dehydratase represents the first committed step in GDP-fucose biosynthesis it is possible that GDP-fucose is a feedback inhibitor of the enzyme. To determine if this is true, the standard assay was performed in the presence of increasing amounts of GDP-fucose. FIG. 5 displays the inhibition curve. It is clear that GDP-fucose is a potent inhibitor of this enzyme with an $IC_{50}$ of approximately 40 µM. This is very important from the standpoint of synthesizing fucosylated oligosaccharides since the synthetic process will require that 1) GDP-fucose is removed from the reaction mixture as would occur with the addition of fucose to an oligosaccharide chain via fucosyltransferase; or 2) that all GDP-mannose is converted to its intermediate, GDP-4-keto-6-deoxymannose prior to conversion into GDP-fucose.

B. Characterization of YEF B, wcaH, and Human Fx Expressed in *E. coli*

1. YEF B Expression

To test for expression, bacteria harboring these plasmids were grown, lysed and analyzed by SDS-PAGE (FIG. 2). These lysates were compared with bacterial lysates harboring the pTGK vector alone (Lane 1). Lysates harboring two separate YEF B clones (Lanes 2 and 3) display highly expressed proteins at 36.5 Kd that are absent in lysates from bacteria harboring the vector alone (Lane 1). The predicted molecular weight of YEF B is 36.5 Kd (Stevenson et al. (1996) *J. Bacteriol.* 178: 4885-4893; Tonetti et al., supra.).

2. wcaH and Human Fx Expression

Figure 6:
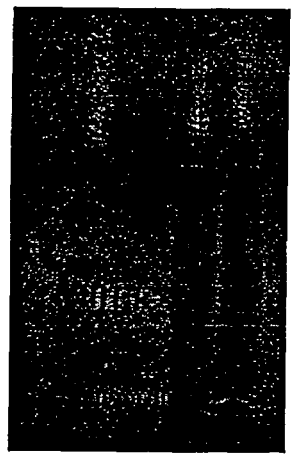
FIG. 6 shows that wcaH and human Fx are expressed by the corresponding expression vectors in *E. coli*. The analysis was performed using 8-15% SDS-PAGE under reducing conditions.

The SDS-PAGE shown in FIG. 6 displays the expression of wcaH and human Fx in *E. coli* from the expression vectors pTGK:wcaH and pTGK:human Fx (pTGK:Fx), respectively. A large band was observed for wcaH. Somewhat unexpectedly, the human Fx protein was also expressed at significant levels in bacteria using this expression system.

3. Assay of YEF B and Human Fx Activity

Figure 7:
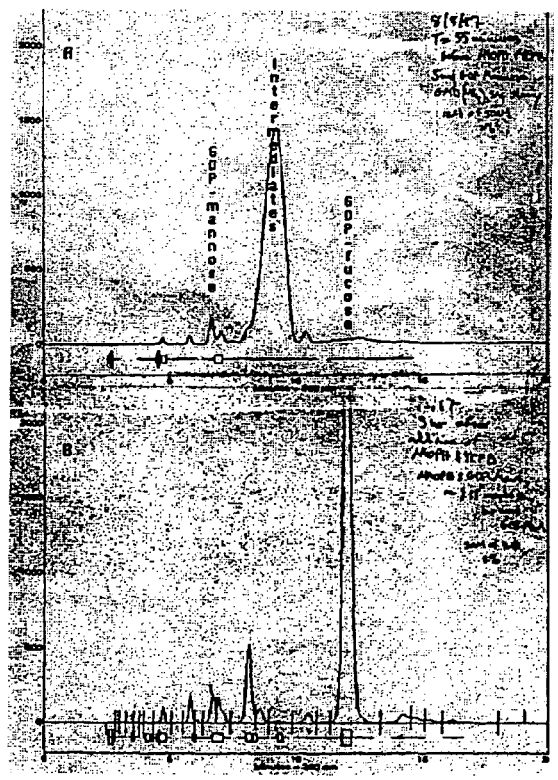
FIG. 7A shows the results of an assay for GDP-mannose dehydratase activity as the first step of a coupled assay for determining the activity of YEF B.
FIG. 7B shows the effect of adding YEF B to the reaction mixture after completion of the GDP-mannose dehydratase reaction.

YEF B and human Fx were assayed using an HPLC method that resolves GDP-mannose from GDP-4-keto-6-deoxymannose, GDP-4-keto-6-deoxyglucose and GDP-fucose based on hydrophobicity as described in methods. FIG. 7A shows the HPLC analysis 55 minutes after addition of GDP-mannose dehydratase. Essentially all the GDP-mannose has been consumed and converted into intermediate products. Upon addition of YEF B and NADPH to this assay mix, a peak with the same absorption spectrum as GDP-fucose and co-migrates with GDP-fucose (FIG. 7B). If an irrelevant extract is used in place of YEF B extract (extract from JM101 cells harboring the pTGK plasmid only) the GDP-fucose absorption peak does not appear.

This indicates that GDP-mannose dehydratase works in conjunction with YEF B to form GDP-fucose. Therefore YEF B, similar to its human homologue, Fx, is both an epimerase and a reductase. Identical results are obtained if YEF B is purified by Cibacron Blue chromatography, providing filter evidence that YEF B encodes both epimerase and reductase activities in a single enzyme.

Human Fx protein also displayed significant activity in this assay, although at levels approximately 10 fold less than YEF B. This mirrors the expression level deduced from SDS-PAGE gels.

4. pH Optimum

The assay pH was varied from 6.5 to 8.0 using MES and Tris as buffers. The standard assay mix contained 20 mUnit GDP-mannose dehydratase, 480 mmole GDP-mannose, 500 mmole glucose, 20 mM $MgCl_2$, 0.2 mM NADPH, 10 mUnit glucose dehydrogenase (to recycle NADPH utilized by YEF B), 50 mM buffer at the appropriate pH and YEF B at appropriate dilution. The reaction was allowed to proceed for 15 minutes at 37° C. and immediately frozen on dry ice to stop the reaction. Ten µl aliquots were removed after thawing and analyzed by reverse phase HPLC. As shown in Table 7, YEF B has a pH optimum of 7.5.

TABLE 7 pH Optimum of YEF B

| pH | Activity (Unit/ml) |
|---|---|
| 6.5 | .83 |
| 7.0 | .91 |
| 7.5 | 1.2 |
| 8.0 | .41 |

5. Metal Ion Requirement

To study the metal ion requirement, standard assay conditions were employed with the addition of varying concentrations of $MgCl_2$ and $MnCl_2$. These two divalent cations were chosen since YEF B can be utilized in a fucose cycle and fucosyltransferase V requires either $MgCl_2$ or $MnCl_2$ for activity. Table 8 displays the results, which show that YEF B is severely inhibited in a dose dependent manner by $MnCl_2$ at concentrations required for fucosyltransferase V activity. In contrast $MgCl_2$ was actually somewhat stimulatory. Thus, the fucose "half cycles" are preferably run in the presence of $MgCl_2$ but not $MnCl_2$.

TABLE 8

Analysis of Metal Ion Effect on YEF B Activity

| [Metal Ion] | Activity % |
|---|---|
| none | 100 |
| 1 mM $MnCl_2$ | 60 |
| 10 mM $MnCl_2$ | 25 |
| 1 mM $MgCl_2$ | 110 |
| 10 mM $MgCl_2$ | 110 |

6. Linearity Over Time

Figure 8:
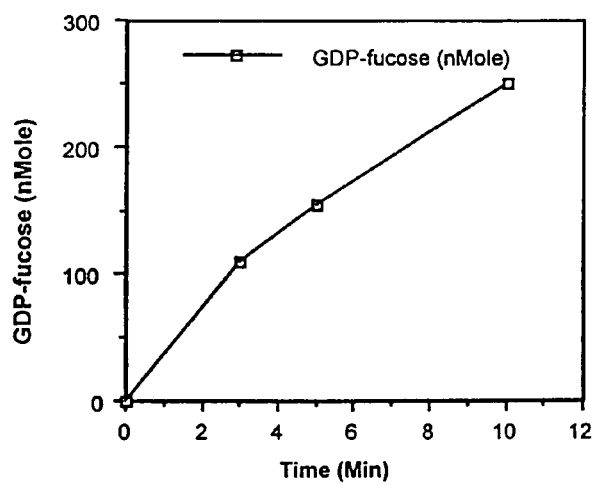
FIG. 8 shows the results of a time course of the coupled GMD-YEF B assay.

To determine the linearity of the coupled YEF B assay over time, standard assay conditions were employed. Ten µl aliquots were removed from the same vial over 30 minutes. A separate tube containing no GDP-mannose dehydratase was used as the 100% control. FIG. 8 displays the results of this assay with respect to time. Although the assay is not linear with respect to time, it does provide an excellent approximation of activity. Likely explanations for the lack of linearity include product inhibition of the epimerization step or reduction step, or both. Regardless, utilizing this assay indicates that a twenty liter fermentation yields 600-700 unit/liter; sufficient for multi kilogram synthesis of sialyl Lewis X antigen or other fucosylated oligosaccharides of interest.

7. Production of GDP-Fucose From GDP-Mannose on a 0.2 kG Scale

To demonstrate that GDP-mannose dehydratase and YEF B can be used to produce GDP-fucose at scale, 200 grams of GDP-mannose was converted into GDP-fucose. This was accomplished using 2000 unit of GDP-mannose dehydratase and 2000 unit of YEF B. To achieve complete conversion of GDP-mannose into its intermediate; GDP-4-keto-6-deoxymannose, YEF B and glucose dehydrogenase must be added after all GDP-mannose has been converted to GDP-4-keto-6-deoxymannose. This is because GDP-fucose, the product of YEF B, is a 40 µM inhibitor of GDP-mannose dehydrogenase (see FIG. 5). Since the GDP-mannose concentration in the reaction mixture is approximately 65 mM, once YEF B is added, along with NADPH and glucose dehydrogenase to recycle NADPH, the conversion of GDP-mannose into its intermediate by GDP-mannose dehydrogenase is halted. Thus the reaction is preferably closely monitored by HPLC to track the amount of GDP-mannose consumed and the amount of GDP-4-keto-6-deoxymannose generated.

Once the GDP-mannose has been completely converted into its intermediate, 2000 unit of YEF B, 900 unit glucose dehydrogenase, 1 gram NADPH and 1.2 molar equivalents of glucose (relative to GDP-mannose) was added to the reaction mixture and incubated overnight at 35° C. The mixture was processed by passing the mixture through a 10 kD MWC tangential flow filtration device to remove the majority of protein and polysaccharide. The GDP-fucose was purified and concentrated by ultrafiltration followed by precipitation by addition of ethanol to 80%. The precipitation step effectively removed free monosaccharides (glucose and gluconate) that were not removed by the ultrafiltration step. On a mole:mole basis this equates to an approximate 65% yield. HPLC analysis was used to confirm that the reaction was complete (FIG. 9).

8. Fucosylation of Sialyl Lewis X Antigen Precursor at the 100 Gram Scale

Figure 10:
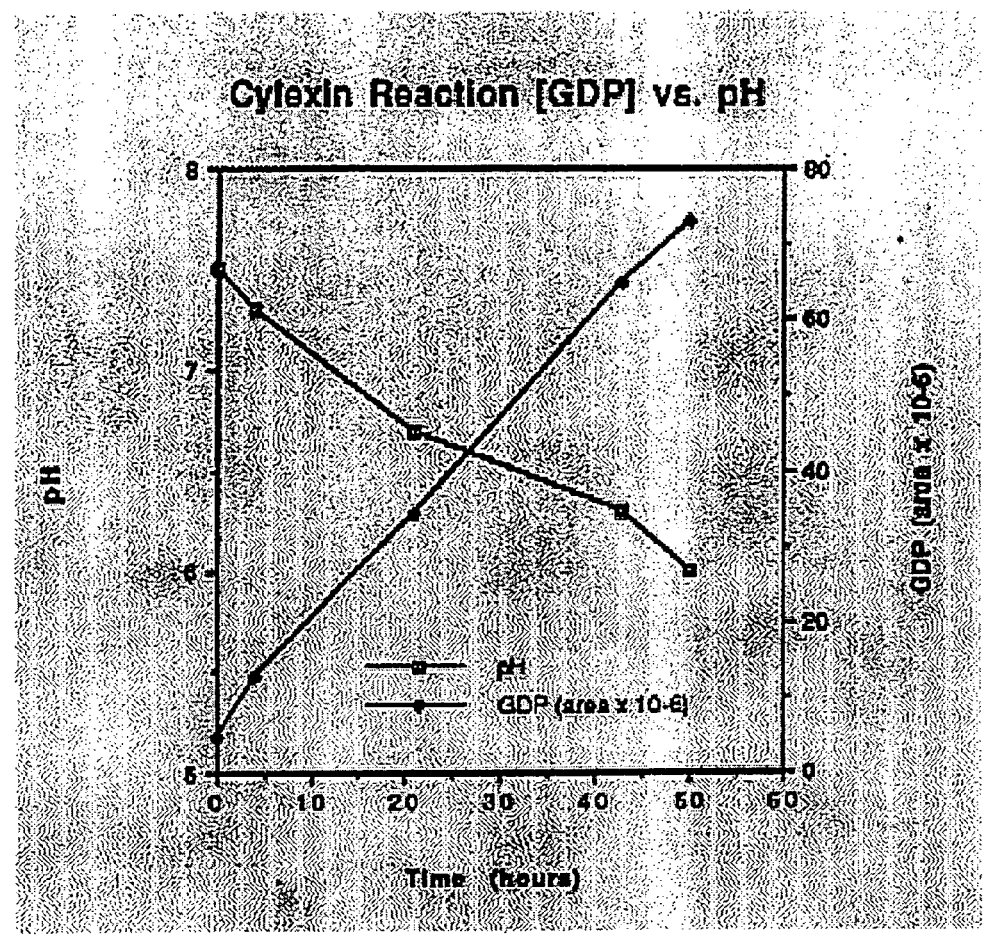
FIG. 10 shows the formation of sialyl Lewis X (as indicated by increasing GDP) over time. The decrease in pH of the reaction mixture that occurs as a result of the reaction is also shown.
Figure 11:
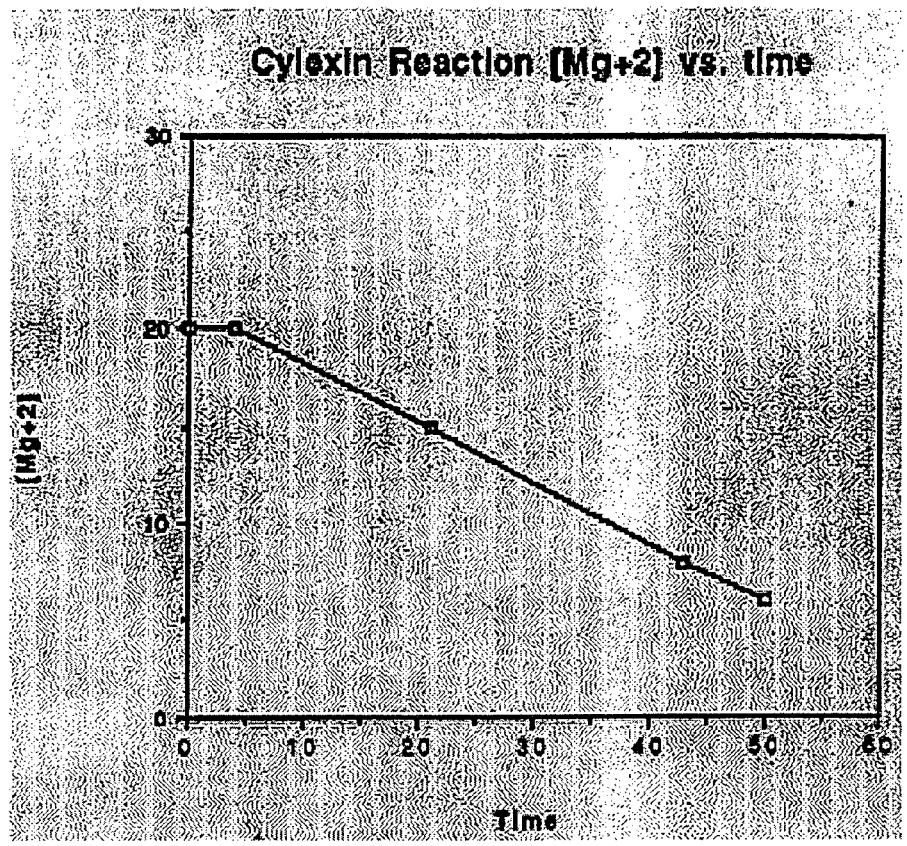
FIG. 11 shows the change in concentration of $Mg^{2+}$ over time during the synthesis of sialyl Lewis X.

To demonstrate the utility of bacterial GDP-mannose dehydratase and YEF B for the large scale synthesis of sialyl Lewis X antigen and other bioactive carbohydrates, a 100 gram reaction was conducted in which Neu5Acα2,3Galβ1,4GlcNAcβ1,3Gal-OR (SLN), the tetrasaccharide precursor of sialyl Lewis X antigen, was fucosylated to form sialyl Lewis X antigen. Conversion of SLN into sialyl Lewis X antigen was monitored by HPLC, TLC and pH by pH electrode. The results of this assay are shown in FIG. 10, in which formation of sialyl Lewis X is monitored by detecting the increase in free GDP concentration. The pH of the reaction mixture is also shown. As GDP was hydrolyzed by alkaline phosphatase liberating inorganic phosphate, the pH of the reaction decreased. The liberated inorganic phosphate also formed a precipitate with magnesium ions, decreasing the concentration of free magnesium, as shown in FIG. 11.

The decrease in pH and magnesium ions dramatically slows the reaction for two reasons: 1) as the pH decreases, the activity of alkaline phosphatase is severely inhibited causing GDP to buildup to levels that inhibit the fucosyltransferase; and 2) fucosyltransferase V requires magnesium at a concentration of 20 mM for optimal activity. Thus as the magnesium concentration decreases, the fucosyltransferase activity also decreases. Therefore, the reaction pH and magnesium concentrations are preferably monitored and the reaction supplemented with $MgCl_2$ and the pH maintained at 8.0 by addition of NaOH. Since calf intestinal phosphatase has a pH optimum of 9.5 and has only 10% of its activity at pH 8.0, a neutral phosphatase (one with a neutral pH activity) is optimal for this reaction.

Figure 12:
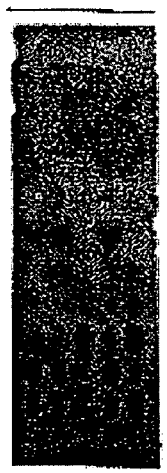
FIG. 12 shows a time course of a large-scale sialyl Lewis X synthesis reaction. Samples were taken from the reaction mixture and analyzed by TLC. From left to right, the lanes are as follows: Lane 1, reaction at 160 hours; Lane 2, 147 hours; Lane 3, SLN; Lane 4, 43 hours; Lane 5, 1 hour.

It is clear from FIG. 12 that the reaction proceeds very rapidly initially, and then slows dramatically. This was due to the buildup of GDP and decrease in magnesium as discussed above. Once the pH was brought up to 8.0 and maintained at this level, and the reaction was supplemented with alkaline phosphatase and magnesium (which was done at 50 hours in this reaction) the reaction proceeds to greater than 95% completion with 15 grams of GDP-fucose added to supplement the reaction.

9. NMR Analysis of Final Sialyl Lewis X Reaction Product at 100 Gram Scale

Figure 13:
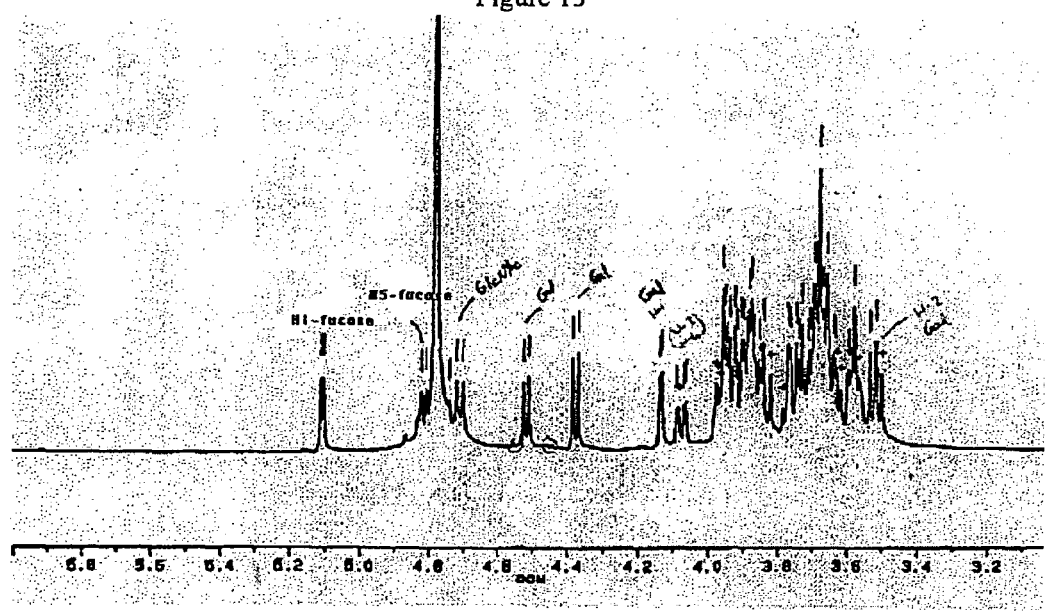
FIG. 13 shows an NMR analysis of the final product obtained in the large-scale fucosylation reaction that used Neu5Acα2,3Galβ1,4GlcNAcβ1,3Gal-OR as a substrate.

The final reaction product was purified by ultrafiltration and subjected to NMR analysis to confirm the addition of fucose to Neu5Acα2,3Galβ1,4GlcNAcβ1,3Gal-OR. FIG. 13 shows the 500 Mhz proton NMR spectra and the pertinent chemical shifts for fucose. The spectrum is identical to authentic sialyl Lewis X antigen and confirms that the concerted action of GDP-mannose dehydratase and YEF B forms GDP-fucose. This donor substrate can then be utilized by fucosyltransferases to synthesize fucosylated oligosaccharides; in this example sialyl Lewis X antigen.

10. Conversion of SLN to Sialyl Lewis X Antigen Using an Enzymatic Half Cycle

Figure 14:
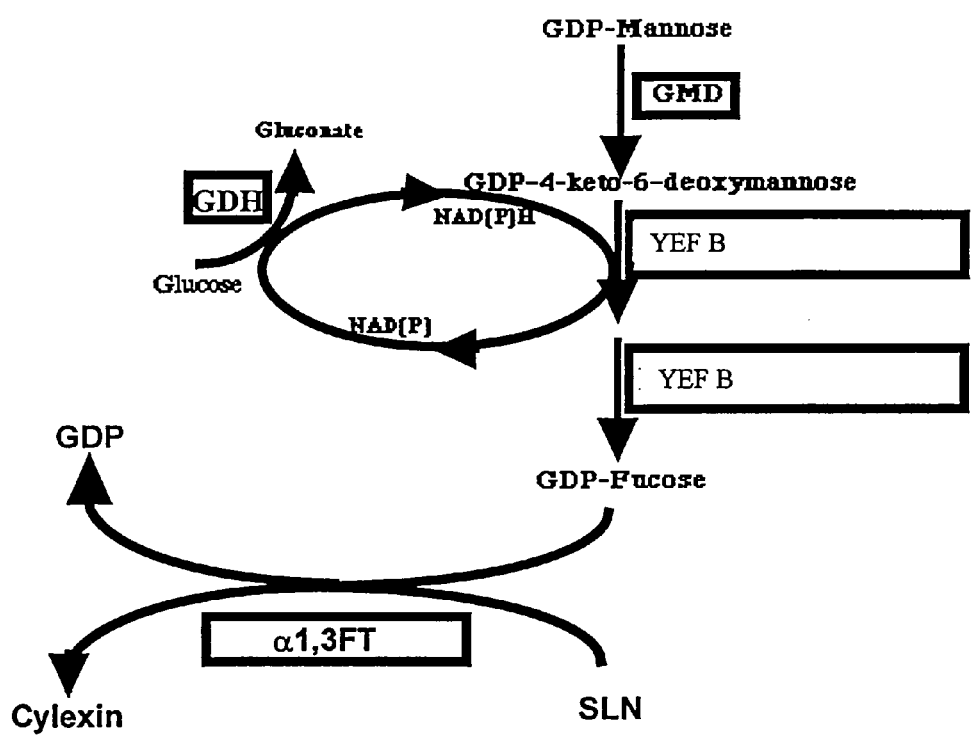
FIG. 14 shows a schematic diagram of a GDP-mannose half-cycle fucosyltransferase reaction.

Previous experiments demonstrated that alkaline phosphatase inactivated GDP-mannose dehydratase by cleavage of its cofactor (NADP) phosphate group (See Table 5). Thus alkaline phosphatase could not be utilized to hydrolyze GDP to its free nucleotide. Removal of GDP is required for this reaction to proceed to completion since GDP is a potent inhibitor of fucosyltransferases (Shinoda et al. (1997) *J. Biol. Chem.* 272: 31992-31997). To accomplish the removal of GDP, conversion of GDP to GTP was tried. GTP is a 10× less potent inhibitor of fucosyltransferase V than GDP. To convert GDP to GTP, PEP and pyruvate kinase were employed in the reaction mixture. The schematic for this GDP-mannose half-cycle fucosyltransferase reaction is shown in FIG. 14. As shown by the TLC in FIG. 15, the reaction consisting of 5 mM SLN and 10 mM GDP-mannose proceeds to approximately 95% completion after 2 days. A 10 fold molar excess of PEP to GDP-mannose was required for completion of this reaction.

Two important results emerge from this experiment: 1) It is possible for the GDP-mannose half cycle to proceed to near completion if GDP is converted to GTP; and 2) strong evidence is provided that a complete cycle starting from mannose with the addition of hexokinase, phosphomannomutase and GDP-mannose pyrophosphorylase, would result in an efficient reaction. See FIG. 15 for an illustration of the full fucosyltransferase cycle, in which GDP-fucose is synthesized from mannose.

It is understood that the examples and embodiments described herein are for illustrative purposes only and that various modifications or changes in light thereof will be suggested to persons skilled in the art and are to be included within the spirit and purview of. this application and scope of the appended claims. All publications, patents, and patent applications cited herein are hereby incorporated by reference for all purposes.

What is claimed is:

1. A method for the preparation of a fucosylated oligosaccharide, the method comprising contacting an acceptor saccharide with a fucosylation reaction mixture that comprises GDP-fucose and a fucosyltransferase which transfers fucose from the GDP-fucose to provide said fucosylated oligosaccharide, wherein the efficiency of said fucosylation is enhanced by forming said GDP-fucose by enzymatic conversion of GDP-mannose to GDP-fucose by:

a) providing a reaction mixture that comprises GDP-mannose, GDP-mannose 4,6-dehydratase, and NADP+;

b) incubating the reaction mixture for a sufficient time to convert at least about 90% of the GDP-mannose to GDP-4-keto-6-deoxymannose;

c) adding to the product of step b) a polypeptide comprising an amino acid sequence with at least 95% identity to SEQ ID NO:1, wherein the polypeptide has GDP-4-keto-6-deoxymannose 3,5-epimerase and GDP-4-keto-6-galactose reductase activities; and d) incubating the reaction mixture for a sufficient time to convert the GDP-4-keto-6-deoxymannose to GDP-fucose.

2. The method of claim 1, wherein the fucosyltransferase is added to the reaction mixture after at least about 90% of the GDP-4-keto-6-deoxymannose is converted to GDP-fucose.

3. The method of claim 1, wherein the fucosyltransferase and the polypeptides having GDP-4-keto-6-deoxymannose 3,5-epimerase and GDP-4-keto-6-galactose reductase are added to the reaction mixture after at least about 90% of the GDP-mannose is converted to GDP-4-keto-6-deoxymannose.

4. The method of claim 1, wherein each of the reaction steps is conducted in the same reaction vessel.

5. The method of claim 1, wherein which method further comprises recycling NADP+ or NAD+ produced by the reductase activity to NADPH or NADH, respectively, by including in the reaction mixture of step c) an enzyme that can reduce the NADP+ or NAD+, and a substrate for the enzyme.

6. The method of claim 5, wherein the enzyme is selected from the group consisting of alcohol dehydrogenase, glucose dehydrogenase, formate dehydrogenase, hydrogenase, and glucose-6-phosphate dehydrogenase.

7. The method of claim 6, wherein the enzyme is glucose dehydrogenase and the substrate is glucose.

8. The method of claim 1, wherein the acceptor saccharide is selected from the group consisting of Galβ(1-4)GlcN(R') β-R and Galβ(1-3)GlcN(R')β-R, wherein R is selected from the group consisting of hydrogen, a saccharide, an oligosaccharide and an aglycon group having at least one carbon atom; and R' is selected from the group consisting of acetyl and allyloxycarbonyl.

9. The method of claim 8, wherein the acceptor saccharide is selected from the group consisting of NeuAcα(2→3)Galβ(1→4)GlcN(R')β(1→3)Galβ-OR and NeuAcα(2→3)Galβ(1→3)GlcN(R')β(1→3)Galβ-OR.

10. The method of claim 9, wherein the acceptor saccharide is formed by sialylating a compound Galβ(1→4)GlcN(R') β(1→3)Galβ-OR or Galβ(1→3)GlcN(R') β(1→3)Galβ-OR with a sialyltransferase in the presence of a CMP derivative of a sialic acid using a α(2,3)sialyltransferase under conditions wherein sialic acid is transferred to the non-reducing sugar of the compound.

11. The method of claim 10, wherein the compound Galβ(1→4)GlcN(R') β(1→3)Galβ-OR or Galβ(1→3)GlcN(R') β(1→3)Galβ-OR is formed by galactosylating a compound of the formula GlcN(R')β(1→3)Galβ-OR or GlcN(R')β(1→3)Galβ-OR, respectively, with a galactosyltransferase in the presence of a UDP-galactose under conditions sufficient to form the compound.

* * * * *

SEQUENCE LISTING

```
<160> NUMBER OF SEQ ID NOS: 9

<210> SEQ ID NO 1
<211> LENGTH: 321
<212> TYPE: PRT
<213> ORGANISM: Escherichia coli
<220> FEATURE:
<223> OTHER INFORMATION: E. coli YEF B

<400> SEQUENCE: 1

Met Ser Lys Gln Arg Val Phe Ile Ala Gly His Arg Gly Met Val Gly
  1               5                  10                  15

Ser Ala Ile Arg Arg Gln Leu Glu Gln Arg Gly Asp Val Glu Leu Val
             20                  25                  30

Leu Arg Thr Arg Asp Glu Leu Asn Leu Leu Asp Ser Arg Ala Val His
         35                  40                  45

Asp Phe Phe Ala Ser Glu Arg Ile Asp Gln Val Tyr Leu Ala Ala Ala
     50                  55                  60

Lys Val Gly Gly Ile Val Ala Asn Asn Thr Tyr Pro Ala Asp Phe Ile
 65                  70                  75                  80

Tyr Gln Asn Met Met Ile Glu Ser Asn Ile Ile His Ala Ala His Gln
                 85                  90                  95

Asn Asp Val Asn Lys Leu Leu Phe Leu Gly Ser Ser Cys Ile Tyr Pro
            100                 105                 110

Lys Leu Ala Lys Gln Pro Met Ala Glu Ser Glu Leu Leu Gln Gly Thr
        115                 120                 125

Leu Glu Pro Thr Asn Glu Pro Tyr Ala Ile Ala Lys Ile Ala Gly Ile
```

-continued

```
            130                 135                 140
Lys Leu Cys Glu Ser Tyr Asn Arg Gln Tyr Gly Arg Asp Tyr Arg Ser
145                 150                 155                 160

Val Met Pro Thr Asn Leu Tyr Gly Pro His Asp Asn Phe His Pro Ser
                165                 170                 175

Asn Ser His Val Ile Pro Ala Leu Leu Arg Arg Phe His Glu Ala Thr
            180                 185                 190

Ala Gln Asn Ala Pro Asp Val Val Trp Gly Ser Gly Thr Pro Met
        195                 200                 205

Arg Glu Phe Leu His Val Asp Asp Met Ala Ala Ser Ile His Val
210                 215                 220

Met Glu Leu Ala His Glu Val Trp Leu Glu Asn Thr Gln Pro Met Leu
225                 230                 235                 240

Ser His Ile Asn Val Gly Thr Gly Val Asp Cys Thr Ile Arg Asp Val
                245                 250                 255

Ala Gln Thr Ile Ala Lys Val Val Gly Tyr Lys Gly Arg Val Val Phe
            260                 265                 270

Asp Ala Ser Lys Pro Asp Gly Thr Pro Arg Lys Leu Leu Asp Val Thr
        275                 280                 285

Arg Leu His Gln Leu Gly Trp Tyr His Glu Ile Ser Leu Glu Ala Gly
        290                 295                 300

Leu Ala Ser Thr Tyr Gln Trp Phe Leu Glu Asn Gln Asp Arg Phe Arg
305                 310                 315                 320

Gly

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:5' PCR
      primer to amplify E. coli GDP-mannose dehydratase (GMD)
      open reading frame

<400> SEQUENCE: 2
cgctctagat acatgtcaaa agtcgct                                     27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:3' PCR
      primer to amplify E. coli GDP-mannose dehydratase (GMD)
      open reading frame

<400> SEQUENCE: 3
gcgaagcttt tatgactcca gcgcgat                                     27

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:5' PCR
      primer to amplify E. coli YEF B open reading frame

<400> SEQUENCE: 4
cgtcctagag cgatgagtaa acaacgagtt                                  30
```

```
<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:3' PCR
      primer to amplify E. coli YEF B open reading frame

<400> SEQUENCE: 5
gcgaagcttt tacccccgaa agcggtc                                         27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:5' PCR
      primer to amplify E. coli Wca H open reading frame

<400> SEQUENCE: 6
gctctagagt aatgatgttt ttacgtcagg                                      30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:3' PCR
      primer to amplify E. coli Wca H open reading frame

<400> SEQUENCE: 7
cccaagcttt cataatccgg gtactccggt                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:5' PCR
      primer to amplify human Fx open reading frame

<400> SEQUENCE: 8
gctctagaga catgggtgaa ccccagggat                                      30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:3' PCR
      primer to amplify human Fx open reading frame

<400> SEQUENCE: 9
acgaagcttc acttccgggc ctgctcgtag ttg                                  33
```